United States Patent
Ikutani et al.

(10) Patent No.: US 10,479,836 B2
(45) Date of Patent: Nov. 19, 2019

(54) METHOD FOR TREATING PULMONARY HYPERTENSION WITH INTERLEUKIN-5 RECEPTOR ANTIBODY

(71) Applicants: University of Toyama, Toyama-shi, Toyama (JP); KYOWA HAKKO KIRIN CO., LTD., Tokyo (JP)

(72) Inventors: Masashi Ikutani, Toyama (JP); Kiyoshi Takatsu, Toyama (JP); Hiromi Ehara, Tokyo (JP); Ikuko Fujino, Tokyo (JP); Shinya Ogawa, Tokyo (JP)

(73) Assignees: National University Corporation University of Toyama, Toyama (JP); KYOWA KIRIN CO., LTD., Tokyo (JP)

(*) Notice: Subject to any disclaimer, the term of this patent is extended or adjusted under 35 U.S.C. 154(b) by 38 days.

(21) Appl. No.: 15/578,864

(22) PCT Filed: May 31, 2016

(86) PCT No.: PCT/JP2016/066015
§ 371 (c)(1),
(2) Date: Dec. 1, 2017

(87) PCT Pub. No.: WO2016/194897
PCT Pub. Date: Dec. 8, 2016

(65) Prior Publication Data
US 2018/0155434 A1 Jun. 7, 2018

(30) Foreign Application Priority Data
Jun. 1, 2015 (JP) ................................ 2015-111395

(51) Int. Cl.
*A61K 39/395* (2006.01)
*C07K 16/28* (2006.01)
*A61P 9/12* (2006.01)
*A61P 11/00* (2006.01)
*A61K 39/00* (2006.01)

(52) U.S. Cl.
CPC ............ *C07K 16/2866* (2013.01); *A61P 9/12* (2018.01); *A61P 11/00* (2018.01); *A61K 2039/505* (2013.01); *C07K 2317/21* (2013.01); *C07K 2317/24* (2013.01); *C07K 2317/41* (2013.01); *C07K 2317/52* (2013.01); *C07K 2317/56* (2013.01); *C07K 2317/565* (2013.01); *C07K 2317/732* (2013.01); *C07K 2317/76* (2013.01)

(58) Field of Classification Search
CPC .............................................. A61K 2039/505
See application file for complete search history.

(56) References Cited

U.S. PATENT DOCUMENTS

| | | | |
|---|---|---|---|
| 6,018,032 A | 1/2000 | Koike et al. | |
| 2014/0255404 A1 | 9/2014 | Lawrie | |

FOREIGN PATENT DOCUMENTS

| | | |
|---|---|---|
| EP | 1 688 437 A1 | 8/2006 |
| JP | 2002-047203 A | 2/2002 |
| JP | 2014-532637 A | 12/2014 |
| JP | 2015-050941 A | 3/2015 |
| JP | 2016-056115 A | 4/2016 |
| WO | 97/10354 A1 | 3/1997 |
| WO | 2005/035583 A1 | 4/2005 |
| WO | 2008/143878 A1 | 11/2008 |
| WO | 2013/066780 A2 | 5/2013 |

OTHER PUBLICATIONS

Werner Seeger et al., "Pulmonary Hypertension in Chronic Lung Diseases", Journal of the American College of Cardiology, 2013, pp. D109-D116, vol. 62, No. 25, Suppl D.
Gerald Maarman et al., "A comprehensive review: the evolution of animal models in pulmonary hypertension research; are we there yet?", Pulmonary Circulation, Dec. 2013, pp. 739-756, vol. 3, No. 4.
Benjamin D. Medoff et al., "Adiponectin Deficiency Increases Allergic Airway Inflammation and Pulmonary Vascular Remodeling", American Journal of Respiratory Cell and Molecular Biology, 2009, pp. 397-406, vol. 41.
M Weng et al., "Eosinophils are necessary for pulmonary arterial remodeling in a mouse model of eosinophilic inflammation-induced pulmonary hypertension", Am. J. Physiol. Lung Cell Mol. Physiol., 2011, pp. L927-L936, vol. 301.
Manali Mukherjee et al., "Anti-IL5 therapy for asthma and beyond", World Allergy Organization Journal, 2014, 15 pages, vol. 7, No. 32.
N.A. Molfino et al., "Molecular and clinical rationale for therapeutic targeting of interleukin-5 and its receptor", Clinical Et. Experimental Allergy, 2010, pp. 712-737, vol. 42.
International Search Report for PCT/JP2016/066015 dated Aug. 2, 2016 [PCT/ISA/210].
Yasumichi Hitoshi et al., "In vivo administration of antibody to murine IL-5 receptor inhibits eosinophilia of IL-5 transgenic mice", International Immunology, vol. 3, No. 2, pp. 135-139, Jan. 1, 1991, 5 pages total.
Masashi Ikutani et al., "Elimination of eosinophils using anti-IL-5 receptor alpha antibodies effectively suppresses IL-33-mediated pulmonary arterial hypertrophy", Immunobiology, vol. 223, pp. 486-492 (2018), 7 pages total.
Extended European Search Report, dated Dec. 20, 2018, issued by the European Patent Office in application No. 16803331.4.

*Primary Examiner* — Prema M Mertz
(74) *Attorney, Agent, or Firm* — Sughrue Mion, PLLC

(57) ABSTRACT

The present invention relates to a therapeutic agent for pulmonary hypertension comprising an interleukin-5 receptor (hereinafter, abbreviated to "IL-5R")-inhibiting compound and therapeutic method therefor. More specifically, the present invention relates to a therapeutic agent for pulmonary hypertension comprising an antibody or an antibody fragment capable of specifically binding to the extracellular region of IL-5R and a therapeutic method therefor.

9 Claims, 14 Drawing Sheets
Specification includes a Sequence Listing.

METHOD FOR TREATING PULMONARY HYPERTENSION WITH INTERLEUKIN-5 RECEPTOR ANTIBODY

CROSS REFERENCE TO RELATED APPLICATIONS

This application is a National Stage of International Application No. PCT/JP2016/066015 filed May 31, 2016, claiming priority based on Japanese Patent Application No. 2015-111395 filed Jun. 1, 2015, the contents of all of which are incorporated herein by reference in their entirety.

TECHNICAL FIELD

The present invention relates to a therapeutic agent for pulmonary hypertension comprising an interleukin-5 receptor (hereinafter, abbreviated to "IL-5R")-inhibiting compound and a therapeutic method therefor. More specifically, the present invention relates to a therapeutic agent for pulmonary hypertension comprising an antibody which specifically binds to the extracellular region of IL-5R or an antibody fragment thereof and a therapeutic method therefor.

BACKGROUND ART

Pulmonary hypertension (PH) is a general term for pathological conditions that manifest a rise in pulmonary arterial pressure. A cause thereof has not yet been identified, though it is known that there are pulmonary hypertensions induced by various causes such as pulmonary hypertension associated with a pre-existing disease including pulmonary diseases such as chronic obstructive pulmonary disease (COPD), idiopathic pulmonary fibrosis (IPF), interstitial pneumonia, and pulmonary emphysema; left heart diseases such as left ventricular failure and valvular disease; systemic diseases such as sarcoidosis, pulmonary Langerhans cell histiocytosis, lymphangioleiomyomatosis, neurofibromatosis, and vasculitis; and primary pulmonary arterial hypertension which originates from pulmonary arteries, etc. (Non Patent Literature 1).

Pulmonary hypertension develops due to a rise in pulmonary arterial pressure resulting from increased vascular resistance in pulmonary arterioles, etc. Pulmonary hypertension is diagnosed when an average pulmonary arterial pressure is 25 mmHg or higher. In chronic pulmonary hypertension, the overload of the right ventricle and right-ventricular failure, which result from progression of pulmonary peripheral vessels remodeling and angiostenosis due to a high pulmonary arterial pressure, cause clinical symptoms such as systemic congestion, breathlessness, easy fatigability, reduced labor power, fainting episodes, ascites, and cyanosis.

The treatment of pulmonary hypertension is performed by vasodilatory therapy using calcium antagonists, prostaglandin $I_2$ analog formulations, nitric oxide (NO) gas, or the like, oxygen therapy, measures to prevent heart failure, anticoagulation therapy with warfarin or the like, and surgical treatment such as lung transplantation.

A plurality of animal models are known for the pathological analysis of pulmonary hypertension or explore therapeutic methods (Non Patent Literature 2). Particularly, a rodent model given interleukin-33 (IL-33) (Patent Literature 1), a rodent model with a particular molecule knocked out (Non Patent Literature 3), and a transgenic rodent model rather caused to express a particular molecule are known for the analysis of the molecular mechanism and are under pathological analysis.

Among others, it is known in the analysis of adiponectin-knockout mice that OVA-induced pulmonary hypertension is caused, leading to vascular remodeling and increased eosinophil infiltration (Non Patent Literature 3). Also, it is known that in the PH models, an anti-interleukin-5 (IL-5) ligand antibody decreases eosinophil infiltration and vascular wall thickening (Non Patent Literature 4).

Therapeutic agents targeting IL-5-IL-5R have been developed in the field of asthma. Anti-IL-5 humanized antibodies mepolizumab (IgG1) and reslizumab (IgG4/κ) and an anti-IL-5Rα antibody benralizumab (MEDI-563) are known (Patent Literatures 2 and 3 and Non Patent Literatures 5 and 6).

CITATION LIST

Patent Literature

Patent Literature 1: Japanese Patent Laid-Open No. 2015-50941
Patent Literature 2: WO1997/10354
Patent Literature 3: WO2005/35583

Non Patent Literature

Non Patent Literature 1: Seeger et al., J. Am. Col. Card., 2013; 62; D109-D116
Non Patent Literature 2: Maarman et al., Pulmonary Circulation, 2013; 3: 739-756
Non Patent Literature 3: Medoff et al., Am J. Resp. Cell Mol. Biol., 2009; 41: 397-406
Non Patent Literature 4: Weng et al., Am. J. Physiol. Lung Cell Mol. Physiol, 2011; 301, L927-936
Non Patent Literature 5: Mukherjee et al., World Allergy Organization J., 2014; 7: 1-14
Non Patent Literature 6: Molfino et al., Clinical Et. Experimental Allergy, 20142, 42: 712-737

SUMMARY OF INVENTION

Technical Problem

Pulmonary hypertension is an acute or chronic disease resulting from an increased vascular pressure in pulmonary arteries or peripheral vessels in lung tissues. In the chronic phase, pulmonary vascular remodeling arises. An object of the present invention is to provide a novel approach for inhibiting and preventing the progression of a pathological condition in pulmonary hypertension and treating the pulmonary hypertension.

Solution to Problem

The inventors have revealed, for the first time, that IL-5-IL-5R signals play an important role in the pathological mechanism of pulmonary hypertension, and found that the inhibition of the signal transduction can inhibit and prevent the progression of a pathological condition in pulmonary hypertension and effectively treat the pulmonary hypertension.

Specifically, the present invention relates to the following (1) to (15).

(1) A therapeutic agent for pulmonary hypertension comprising an antibody or an antibody fragment thereof which binds to the extracellular region of an interleukin-5 receptor (IL-5R).

(2) The therapeutic agent according to (1), wherein the antibody removes an IL-5R-expressing cell.

(3) The therapeutic agent according to (1) or (2), wherein the antibody has antibody-dependent cellular cytotoxic activity (ADCC activity).

(4) The therapeutic agent according to any of (1) to (3), wherein the antibody has IL-5R-neutralizing activity.

(5) The therapeutic agent according to any of (1) to (4), wherein the antibody inhibits group 2 innate lymphoid cell (ILC2)-dependent IL-5R-expressing cell growth.

(6) The therapeutic agent according to any of (1) to (5), wherein the antibody is any one antibody selected from a monoclonal antibody and a recombinant antibody.

(7) The therapeutic agent according to any of (1) to (6), wherein the antibody comprises a human Fc region or a human constant region.

(8) The therapeutic agent according to any of (1) to (7), wherein the antibody is any one antibody selected from a chimeric antibody, a humanized antibody, and a human antibody.

(9) A method for treating pulmonary hypertension, comprising administering an antibody or an antibody fragment thereof which binds to the extracellular region of an interleukin-5 receptor (IL-5R) to inhibit an IL-5R-expressing cell.

(10) The method according to (9), wherein the antibody removes an IL-5R-expressing cell.

(11) The method according to (9) or (10), wherein the antibody has antibody-dependent cellular cytotoxic activity (ADCC activity).

(12) The method according to any of (9) to (11), wherein the antibody has IL-5R-neutralizing activity.

(13) The method according to any of (9) to (12), wherein the antibody inhibits group 2 innate lymphoid cell (ILC2)-dependent IL-5R-expressing cell growth.

(14) The method according to any of (9) to (13), wherein the method is characterized by at least one of the following (i) to (iii):
(i) the IL-5R-expressing cell is at least one cell of an eosinophil, a basophil, and a mast cell;
(ii) the method inhibits the growth of a vascular smooth muscle cell; and
(iii) the method inhibits pulmonary vascular remodeling.

(15) The therapeutic agent according to any of (1) to (8), wherein the therapeutic agent is characterized by at least one of the following (i) to (iii):
(i) the IL-5R-expressing cell is at least one cell of an eosinophil, a basophil, and a mast cell;
(ii) the therapeutic agent inhibits the growth of a vascular smooth muscle cell; and
(iii) the therapeutic agent inhibits pulmonary vascular remodeling.

Advantageous Effects of Invention

The present invention provides a novel approach for treating pulmonary hypertension, targeting the IL-5-IL-5R signal transduction system. The therapeutic agent and the therapeutic method of the present invention can inhibit the growth of a vascular smooth muscle cell and pulmonary vascular remodeling and effectively treat pulmonary hypertension, by inhibiting IL-5-IL-5R signal transduction using an antibody or an antibody fragment thereof which specifically binds to the extracellular region of IL-5R.

DESCRIPTION OF EMBODIMENTS

Figure 1:
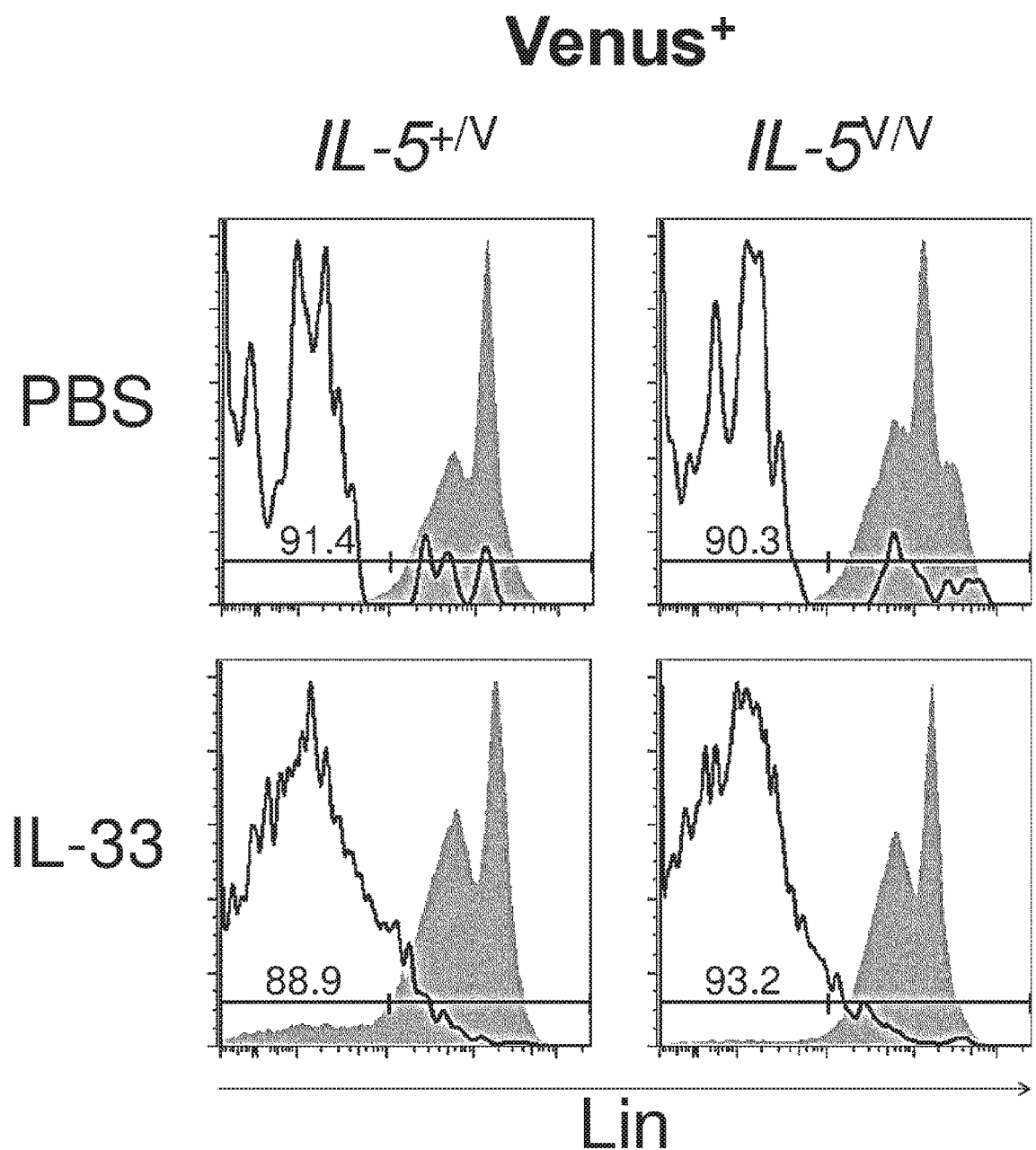
FIG. 1 shows the percentage (%) of blood cell lineage (Lin) marker-negative cells in the Venus-positive cells of IL-$5^{+/Venus(V)}$ mice and IL-$5^{V/V}$ (IL-5-deficient) mice to which PBS or IL-33 was administered weekly for 3 weeks. The white histograms show Venus-positive cells, and the gray histograms show Venus-negative cells. In each graph, the ordinate depicts a cell number, and the abscissa depicts a Lin expression level.

The present invention relates to a therapeutic agent for pulmonary hypertension comprising an interleukin-5 receptor (IL-5R)-inhibiting compound and a therapeutic method therefor. Specifically, the present invention relates to a therapeutic agent for pulmonary hypertension comprising an antibody or an antibody fragment thereof which specifically binds to the extracellular region of IL-5R and a therapeutic method therefor.

In the present invention, the "pulmonary hypertension" may be primary in the lungs, may be secondary, or may be complicated with another disease as long as the pulmonary hypertension manifests a pathological condition with an increased pulmonary arterial pressure. The secondary pulmonary hypertension may involve an underlying disease or may be diagnosed at the same time with an underlying disease.

The primary pulmonary hypertension is major pulmonary arterial hypertension (PAH) and is induced by various causes. PAH is further classified into idiopathic pulmonary arterial hypertension (idiopathic PAH), heritable pulmonary arterial hypertension (heritable PAH), drug- and toxicity-induced pulmonary arterial hypertension, pulmonary arterial hypertension associated with, for example, connective tissue disease, HIV infection, and congenital heart disease, and the like.

Examples of the secondary pulmonary hypertension include: pulmonary hypertension associated with left heart diseases such as left ventricular failure, valvular disease, and congenital heart disease; pulmonary hypertension associated with chronic obstructive pulmonary disease (COPD), interstitial pneumonia, pulmonary emphysema, sleep-related breathing disorder, alveolar hypoventilation syndrome, development disorder, and the like; and pulmonary hypertension associated with chronic thromboembolic hypertension, chronic hemolytic anemia, myeloproliferative disease, sarcoidosis, pulmonary Langerhans cell histiocytosis, lymphangioleiomyomatosis, vasculitis, diabetes mellitus, Gaucher disease, thyroid gland disease, chronic renal failure, and the like.

In the present invention, the "IL-5R-inhibiting compound" can be any compound that blocks the signal transduction between IL-5 and IL-5R and neutralizes or inhibits the biological activity of IL-5, and may be a low-molecular compound or a high-molecular compound.

Examples of the "IL-5R-inhibiting compound" include IL-5 antagonists, IL-5R antagonists, an antibody inhibiting the binding between IL-5 and IL-5R and an antibody fragment thereof, an IL-5-neutralizing antibody and a fragment of the antibody, and an IL-5R-neutralizing antibody and an antibody fragment thereof.

Examples of the antibody inhibiting the binding between IL-5 and IL-5R include an antibody that binds to IL-5 and inhibits the binding between the IL-5 and IL-5R, and an antibody that binds to an IL-5 receptor and inhibits the binding between IL-5 and the IL-5R (anti-IL-5R antibody). Preferred examples thereof include an antibody inhibiting IL-5R signals as a result of inhibiting the binding between IL-5 and IL-5R.

Examples of the antibody inhibiting IL-5R signals through binding to IL-5 include an anti-human IL-5 humanized antibody mepolizumab (IgG1) and an anti-human IL-5 antibody reslizumab (IgG4/κ).

Examples of the antibody inhibiting IL-5R signals through binding to IL-5R include an antibody comprising the complementarity determining regions (CDRs) of an anti-IL-5R rat monoclonal antibody H7 (Hitoshi et al., Int. Immunol., 1991, 3: 135-139), an antibody binding to the same epitope as for the H7 antibody, an antibody binding to the same epitope as for an anti-human IL-5Rα antibody benralizumab, an antibody comprising the CDRs of the anti-human IL-5Rα antibody benralizumab, an antibody comprising the heavy chain variable region (VH) and light chain variable region (VL) of the anti-human IL-5Rα antibody benralizumab, and the anti-human IL-5Rα antibody benralizumab. The anti-IL-5R antibody acts directly on an IL-5R-expressing cell and inhibits IL-5R-dependent signals. Consequently, the cell growth inhibition, migration inhibition, and/or apoptosis induction of the IL-5R-expressing cell can be caused, while the IL-5R-expressing cell can be removed by effector activity such as antibody-dependent cellular cytotoxic activity (ADCC activity). Therefore, the anti-IL-5R antibody is more preferred as the IL-5R-inhibiting compound.

IL-5R is composed of two types of polypeptide chains: an α chain (hereinafter, referred to as an "IL-5Rα chain") and a β chain (hereinafter, referred to as an "IL-5Rβ chain"). The IL-5Rα chain is responsible for binding to IL-5, and the IL-5Rβ chain alone does not exhibit the ability to bind to IL-5. Thus, the antibody used in the present invention is preferably an antibody binding to the IL-5Rα chain.

An anti-IL-5R antibody used in the present invention is preferably an antibody that recognizes the "extracellular region" of IL-5R, which is involved in the binding between IL-5 and the IL-5R, as an epitope. Examples of such an epitope include an epitope present in an amino acid sequence from positions 1 to 313 of the extracellular region that lacks the transmembrane region of IL-5Rα and its downstream region and corresponds to N-terminal amino acids, an epitope present in an amino acid sequence from positions 41 to 61 of the extracellular region of IL-5Rα, an epitope present in an amino acid sequence from positions 52 to 61 of the extracellular region of IL-5Rα, an epitope containing the 61st amino acid residue of the extracellular region of IL-5Rα, and an epitope to which an anti-human IL-5Rα antibody benralizumab binds (Kolbeck et al., J. Allergy Clin. Immunol., 2010, 125: 1344-1353).

The antibody used in the present invention may be a monoclonal antibody or a polyclonal antibody and is preferably a monoclonal antibody binding to a single epitope.

The monoclonal antibody may be any monoclonal antibody that is a monoclonal antibody produced from a hybridoma or a recombinant antibody prepared by a gene recombination technology.

The antibody used in the present invention is preferably a recombinant antibody such as an antibody comprising a human Fc region, an antibody comprising a human constant region, a human-type chimeric antibody (hereinafter, also simply referred to as a chimeric antibody), a humanized antibody [also called a human-type complementarity determining region (CDR)-grafted antibody], or a human antibody, for reducing immunogenicity in humans.

A chimeric antibody is an antibody composed of the heavy chain variable region (hereinafter, abbreviated to VH) and light chain variable region (hereinafter, abbreviated to VL) of a non-human animal antibody, and the heavy chain constant region (hereinafter, abbreviated to CH) and light chain constant region (hereinafter, abbreviated to CL) of a human antibody. The type of the animal as to the variable regions is not particularly limited as long as the animal is capable of producing a hybridoma, such as a mouse, a rat, a hamster, or a rabbit.

A human-type chimeric antibody can be prepared by obtaining cDNAs encoding VH and VL of a non-human animal antibody specifically binding to human IL-5R, and respectively inserting the cDNAs to expression vectors having genes encoding CH and CL of a human antibody to construct human-type chimeric antibody expression vectors, which are then transferred to animal cells, followed by expression.

A CH of the human-type chimeric antibody is not particularly limited as long as the CH is derived from a human immunoglobulin (hereinafter, abbreviated to hIg). CH of hIgG class is preferred. The CL of the human-type chimeric antibody is not particularly limited as long as the CL belongs to hIgG.

A humanized antibody is an antibody comprising the VH and VL CDRs of a non-human animal antibody grafted at appropriate positions of the VH and VL of a human antibody. The humanized antibody can be prepared by constructing cDNAs encoding variable regions (hereinafter, abbreviated to V regions) in which VH and VL CDRs of a non-human animal antibody specifically binding to IL-5R are grafted in VH and VL framework regions (hereinafter, abbreviated to FRs) of an arbitrary human antibody, and respectively inserting the cDNAs to expression vectors having DNAs encoding CH and CL of a human antibody to construct humanized antibody expression vectors, which are then transferred to animal cells, followed by expression. The amino acid sequences of VH and VL FRs of a human antibody are not particularly limited as long as the amino acid sequences are derived from a human antibody. The CH of a humanized antibody is not particularly limited as long as the CH is derived from hIg. CH of hIgG class is preferred. The CL of a humanized antibody is not particularly limited as long as the CL belongs to hIg.

An "antibody fragment" used in the present invention is not particularly limited as long as it is a fragment of each antibody described above and inhibits IL-5R signals through binding to IL-5 or IL-5R. Examples of the type of the antibody fragment include Fab, Fab', F(ab')$_2$, scFv, diabody, dsFv, and a CDR-containing peptide.

A Fab is an antibody fragment with a molecular weight of approximately 50,000 having antigen binding activity, among fragments obtained by treating IgG with papain (proteolytic enzyme). A Fab of an anti-IL-5R antibody can be prepared by treating the anti-IL-5R antibody with papain, or by inserting DNA encoding the Fab of an antibody to an expression vector, and transferring this vector to a prokaryote or a eukaryote, followed by expression.

A F(ab')$_2$ is an antibody fragment with a molecular weight of approximately 100,000 having antigen binding activity, among fragments obtained by treating IgG with pepsin (proteolytic enzyme). A F(ab')$_2$ of an anti-IL-5R antibody can be prepared by treating the anti-IL-5R antibody with pepsin, or by joining together Fab' (mentioned later) fragments via a thioether bond or a disulfide bond.

A Fab' is an antibody fragment with a molecular weight of approximately 50,000 having antigen binding activity obtained by cleaving the disulfide bonds in the hinge region of F(ab')$_2$. A Fab' of an anti-IL-5R antibody can be prepared by treating A F(ab')$_2$ of an anti-IL-5R antibody with dithiothreitol, or by inserting DNA encoding the Fab' of an antibody to an expression vector, and transferring this vector to a prokaryote or a eukaryote, followed by expression.

An scFv is an antibody fragment having antigen binding activity in which one VH and one VL are linked using an appropriate peptide linker. An scFv of an anti-IL-5R antibody can be prepared by obtaining cDNAs encoding the VH and VL of the anti-IL-5R antibody to construct DNA encoding the scFv, inserting this DNA to an expression vector, and transferring this expression vector to a prokaryote or a eukaryote, followed by expression.

A diabody is an antibody fragment composed of dimerized scFvs and is an antibody fragment having divalent antigen binding activity. A diabody of an anti-IL-5R antibody can be prepared by obtaining cDNAs encoding the VH and VL of the anti-IL-5R antibody to construct DNA encoding the diabody, inserting this DNA to an expression vector, and transferring this expression vector to a prokaryote or a eukaryote, followed by expression.

A dsFv is an antibody fragment in which VH and VL polypeptides each having a cysteine residue replaced for one amino acid residue are joined together via the disulfide bond between the cysteine residues. A dsFv of an anti-IL-5R antibody can be prepared by obtaining cDNAs encoding the VH and VL of the anti-IL-5R antibody to construct DNA encoding the dsFv, inserting this DNA to an expression vector, and transferring this expression vector to a prokaryote or a eukaryote, followed by expression.

A CDR-containing peptide is a peptide containing at least one or more of VH or VL CDR regions. A CDR-containing peptide of an anti-IL-5R antibody can be prepared by constructing DNA encoding the VH or VL CDR of the anti-IL-5R antibody, inserting this DNA to an expression vector, and transferring this expression vector to a prokaryote or a eukaryote, followed by expression. Also, the CDR-containing peptide of the anti-IL-5R antibody can be prepared by a chemical synthesis method such as Fmoc method (fluorenylmethyloxycarbonyl method) or tBoc method (t-butyloxycarbonyl method). A peptide containing 6 CDRs derived from the anti-IL-5R antibody is preferred.

The antibody used in the therapeutic agent and the therapeutic method of the present invention preferably has effector activity. The "effector activity" is an activity that is induced via the Fc region of the antibody. For example, antibody-dependent cellular cytotoxic activity (ADCC activity), complement-dependent cytotoxic activity (CDC activity), and antibody-dependent phagocytosis (ADP activity) by phagocytes such as macrophages or dendritic cells are known.

For example, a method of controlling the amount of α1-6-linked fucose (also called core fucose) on N-acetylglucosamine (GlcNAc) at the reducing end of an N-linked complex-type sugar chain linked to asparagine (Asn) 297 (based on the EU index (Kabat et al., Sequence of Proteins of immunological interests, 5th edition, 1991) of the Fc region of an antibody (International Publication Nos. WO 2005/035586, WO 2002/31140, and WO 00/61739) or a control method by altering an amino acid residue in the Fc region of the antibody is known as a method for controlling the effector activity.

An effector activity of an antibody can be increased or decreased by controlling the content of the core fucose on a N-linked complex-type sugar chain linked to the Fc of the antibody. A method for decreasing the content of fucose bound to an N-linked complex-type sugar chain linked to the Fc of the antibody by expressing the antibody using CHO cells in which α1,6-fucosyltransferase (fucosyltransferase-8, FUT8) gene is lacked can be used to obtain an afucosylated antibody.

An afucosylated antibody has high ADCC activity. On the other hand, one embodiment of a method for increasing the content of the fucose bound to an N-linked complex-type sugar chain linked to the Fc of the antibody is as following. For example, host cells transfected with α1,6-fucosyltransferase gene can be used to express the antibody in order to obtain a fucosylated antibody. The fucosylated antibody has lower ADCC activity than that of the afucosylated antibody.

The ADCC activity or the CDC activity can be increased or decreased by altering an amino acid residue in the Fc region of an antibody. An amino acid residue alteration of the Fc region can increase or decrease binding activity against FcγR and thereby control the ADCC activity. The amino acid residue alteration of the Fc region can increase or decrease binding activity against a complement and thereby control the CDC activity.

The CDC activity of the antibody can be increased by using, for example, the amino acid sequence of a Fc region described in the specification of U.S. Patent Application Publication No. 2007/0148165. Also, the ADCC activity or the CDC activity can be increased or decreased by performing amino acid residue alteration described in the specifications of U.S. Pat. Nos. 6,737,056, 7,297,775, 7,317,091, and International Publication No. WO 2005/070963.

The antibody used in the present invention preferably has high ADCC activity or CDC activity, particularly, high ADCC activity, by the alteration mentioned above.

Preferred examples of the antibody used in the present invention include an anti-IL-5R antibody binding to an epitope contained in positions 1 to 313 from the N terminus of the IL-5Rα protein, an anti-IL-5R antibody having ADCC activity through binding to the epitope, an anti-IL-5R antibody binding to an epitope present at positions 41 to 61 of the IL-5Rα protein, an anti-IL-5R antibody binding to an epitope present at positions 52 to 61 of the IL-5Rα protein, an anti-IL-5R antibody binding to Ile 61 of the IL-5Rα protein, an antibody binding to an epitope on IL-5Rα present in the IL-5-binding moiety of the IL-5Rα, an anti-IL-5R antibody comprising heavy chain (H chain) CDR1 to CDR3 respectively comprising the amino acid sequences represented by SEQ ID NOs: 1 to 3 and light chain (L chain) CDR1 to CDR3 respectively comprising the amino acid sequences represented by SEQ ID NOs: 4 to 6, an anti-IL-5R antibody comprising VH comprising the amino acid sequence represented by SEQ ID NO: 7 and VL comprising the amino acid sequence represented by SEQ ID NO: 8, an antibody comprising an H chain comprising the amino acid sequence represented by SEQ ID NO: 9 and a L chain comprising the amino acid sequence represented by SEQ ID NO: 10, an antibody comprising the CDRs of an anti-human IL-5Rα antibody benralizumab, and an antibody comprising the VH and VL of the anti-human IL-5Rα antibody benralizumab. Also, an antibody which has a decreased content of the aforementioned core fucose linked to the N-glycoside-linked sugar chain at position 297 of the Fc region of an antibody or which lacks this core fucose is preferred. Still more specific examples thereof include the anti-IL-5R humanized antibody benralizumab. One example includes a recombinant antibody, a human-type chimeric antibody, a humanized antibody, and a human antibody comprising the CDRs of an anti-IL-5R rat antibody H7 (its gene and amino acid sequences are shown in SEQ ID NOs: 13 to 18).

The antibody used in the present invention is preferably an antibody in which the degree of afucosylation on the aforementioned N-glycoside complex-type sugar chain linked to the Fc region of the above-mentioned antibody is 80% or more, 90% or more, preferably 91%, 92%, 93%, 94%, or 95% or more, more preferably an afucosylated antibody lacking the linked fucose on the sugar chain. This can be expected to perform high ADCC activity.

The antibody used in the present invention may be an antibody comprising an amino acid sequence comprising alteration of the aforementioned amino acid sequence in order to improve the physical properties of the antibody. One example includes antibodies H7-2 (H7 (CS) hIgG1 (DF) and H7-4 (H7 (CS) hIgG1 (N297A)) comprising a light chain variable region (VL) consisting of an amino acid sequence comprising the replacement of the amino acid sequence of the VL of an anti-IL-5R rat antibody H7 in the neighborhood of CDR3, specifically, a Cys residue present at position 87 from the N terminus, with a Ser residue (amino acid sequence encoded by the nucleotide sequence represented by SEQ ID NO: 26).

The anti-IL-5R antibody and the antibody fragment thereof used in the present invention can be produced with reference to WO1997/10354 and WO2005/35583 described above.

The antibody used in the present invention can inhibit IL-5-dependent IL-5R signals through specific binding to an "IL-5R-expressing cell" and thereby inhibit IL-5-dependent cell growth, differentiation induction, migration activity, infiltration activity, and anti-apoptosis activity. Also, the antibody can induce apoptosis of the IL-5R-expressing cell under IL-5-dependent cell growth. Furthermore, the antibody can efficiently remove the IL-5R-expressing cell by ADCC activity.

Examples of the "IL-5R-expressing cell" include an eosinophil, a basophil, and a mast cell (Kolbeck et al., J. Allergy Clin. Immunol., 2010, 125: 1344-1353). The antibody used in the present invention binds to IL-5R on any of these cells, preferably, the eosinophil or both of the eosinophil and the basophil, and exhibits IL-5-dependent cell growth, differentiation induction, migration activity, infiltration activity, and/or anti-apoptosis activity.

The "IL-5R-expressing cell" migrates to the peripheral region of pulmonary blood vessels via group 2, innate lymphoid cell (ILC2)-dependent IL-5 and causes inflammatory reaction, vascular wall thickening, and pulmonary vascular remodeling. Accordingly, the antibody according to the present invention inhibits and prevents such inflammatory reaction, vascular wall thickening, and pulmonary vascular remodeling.

The anti-IL-5R antibody used in the present invention binds not only to the eosinophil but to both of the eosinophil and basophil and thereby inhibits IL-5-dependent IL-5Rα signals while inhibiting both of the cells by ADCC activity and apoptosis-inducing activity (Molfino et al., Clin. Et.

Experimental Allergy, 2011, 42: 712-737). Thus, the anti-IL-5R antibody used in the present invention can inhibit mechanisms underlying the progression and worsening of a pathological condition of pulmonary hypertension in which both of the cells are involved.

The anti-IL-5R antibody used in the present invention can inhibit ILC2-dependent IL-5R-expressing cell growth. This inhibition of the cell growth may be any of the inhibition of IL-5R-dependent cell growth as a result of inhibiting IL-5-IL5R signals, the inhibition of cell growth by inducing apoptosis as a result of the binding of the anti-IL-5R antibody to IL-5R, and the inhibition of cell growth by cytotoxic activity caused by effector activity such as ADCC activity as a result of the binding of the IL-5R antibody to IL-5R.

The therapeutic agent of the present invention may use the IL-5R-inhibiting compound (particularly, the anti-IL-5R antibody or the antibody fragment thereof) in combination with an additional therapeutic agent or therapy. The IL-5R-inhibiting compound can be used in combination with, for example, vasodilatory therapy using calcium antagonists, endothelin receptor (ETR) antagonists, prostaglandin $I_2$ (prostacyclin) analog formulations, cGMP inhibitors, nitric oxide (NO) gas, or the like, oxygen therapy, measures to prevent heart failure, or anticoagulation therapy with warfarin or the like. In this case, the anti-IL-5R-inhibiting compound and the additional therapeutic agent or therapy may be administered or used in treatment simultaneously or may be administered or used in treatment continuously.

The therapeutic agent for pulmonary hypertension of the present invention can be any pharmaceutical composition containing the aforementioned IL-5R-inhibiting compound (particularly, the anti-IL-5R antibody or the antibody fragment thereof) as an active ingredient. It is usually desirable that the therapeutic agent should be provided as a pharmaceutical preparation produced by mixing the active ingredient with one or more pharmaceutically acceptable carriers according to an arbitrary method well known in the field of pharmaceutical technology.

Preferably, a sterile solution of the active ingredient dissolved in an aqueous carrier such as water or an aqueous solution of common salt, glycine, glucose, human albumin, or the like is used. Also, the preparation solution can be supplemented with a pharmaceutically acceptable additive such as a buffering agent or a tonicity agent, for example, sodium acetate, sodium chloride, sodium lactate, potassium chloride, or sodium citrate, in order to achieve conditions close to physiological conditions. Alternatively, the preparation may be stored in a freeze-dried form and dissolved in an appropriate solvent upon use.

A route most effective for treatment is preferably used as the administration route of the therapeutic agent of the present invention. Examples thereof can include oral administration, and parenteral administration such as administration into the oral cavity, administration into the airway, intrarectal administration, subcutaneous administration, intramuscular administration, intrathecal administration, and intravenous administration. Intrathecal administration or intravenous administration is preferred.

Examples of the preparation appropriate for oral administration include emulsions, syrups, capsules, tablets, powders, and granules. For example, the liquid preparations such as emulsions and syrups can be produced using additives including water, saccharides such as sucrose, sorbitol, and fructose, glycols such as polyethylene glycol and propylene glycol, oils such as sesame oil, olive oil, and soybean oil, antiseptics such as p-hydroxybenzoic acid esters, and flavors such as strawberry flavor and peppermint.

The capsules, the tablets, the powders, or the granules, etc. can be produced using additives including excipients such as lactose, glucose, sucrose, and mannitol, disintegrants such as starch and sodium alginate, lubricants such as magnesium stearate and talc, binders such as polyvinyl alcohol, hydroxypropylcellulose, and gelatin, surfactants such as fatty acid esters, and plasticizers such as glycerin.

Examples of the preparation appropriate for parenteral administration include injections, suppositories, and aerosolized agents. The injections are prepared using, for example, a carrier composed of a salt solution, a glucose solution, or a mixture thereof. The suppositories are prepared using a carrier such as cacao butter, hydrogenated fatty or carboxylic acid. The aerosolized agents are prepared using the antibody either alone or together with a carrier or the like that facilitates dispersing the antibody as fine particles and absorbing the antibody without irritating the oral cavity and the mucous membrane of the respiratory tract in a recipient.

Specific examples of the carrier include lactose and glycerin. Preparations such as aerosols or dry powders are possible depending on the properties of the antibody and the carrier used. These parenteral agents may be supplemented with components listed as the examples of additives for the oral agents.

The dose or the number of doses of the therapeutic agent of the present invention differs depending on intended therapeutic effects, an administration method, a treatment period, age, body weight, etc. The dose is usually 1 µg/kg to 10 mg/kg per day in an adult. Specific examples thereof include administration at a single dose of 10 to 600 mg (flat volume) every 4 weeks (Q4W) or 8 weeks (Q8W). More specific examples thereof include administration at a single dose of 30 mg, 60 mg, 100 mg, or 200 mg every 4 weeks or 8 weeks.

For example, IL-5-dependent cell growth, the cell growth, migration, or infiltration of IL-5R-expressing cells, inflammation, leukocyte infiltration, fibrosis, and scarring in lung tissues, and decrease in intravascular lumen, vascular blockage, thrombus, inflammation, vascular smooth muscle cell growth, vascular wall swelling, thickening, leukocyte infiltration, fibrosis, and pulmonary vascular remodeling in pulmonary blood vessels, pulmonary arteries, or pulmonary arterioles are known as mechanisms related to the development and/or worsening of pulmonary hypertension.

The "pulmonary vascular remodeling" refers to a phenomenon in which intravascular lumens are decreased or blocked as a result of causing vascular wall swelling, thickening, fibrosis, etc. due to the growth, hypertrophy, differentiation, or the like of pulmonary arterial smooth muscle cells attributed to inflammation or the like in the vascular endothelium, the media of vessels, or perivascular regions.

The therapeutic agent of the present invention can inhibit the growth of a vascular smooth muscle cell and inhibit pulmonary vascular remodeling in pulmonary hypertension, by inhibiting the growth of an IL-5R-expressing cell. Thus, the therapeutic agent can inhibit serious pulmonary vascular wall thickening and inflammation.

The present invention also provides a method for treating pulmonary hypertension, comprising inhibiting an IL-5R-expressing cell by administering the IL-5R-inhibiting compound of the present invention, particularly, the aforementioned antibody or the antibody fragment thereof which binds to the extracellular region of IL-5R.

The therapeutic method of the present invention directly inhibits ILC2-mediated eosinophil migration by inhibiting IL-5-IL-5R signal transduction. Thus, the therapeutic method inhibits subsequent inflammatory reaction in the peripheral region of pulmonary blood vessels, pulmonary vascular wall thickening, and pulmonary vascular remodeling and treats pulmonary hypertension.

EXAMPLES

Hereinafter, the present invention will be described in more detail with reference to Examples. However, the present invention is not intended to be limited by these Examples.

Example 1

IL-33-Induced Pulmonary Arterial Wall Thickening and Perivascular IL-5-Dependent Eosinophilic Inflammation In this Example, wild-type C57BL/6 mice (IL-5$^{+/+}$) (Japan SLC, Inc.), and heterozygous knockout mice (also referred to as IL-5$^{+/Venus}$ or IL-5$^{+/V}$) and homozygous knockout mice (IL-5$^{V/V}$) (Ikutani et al., J. Immunol., 2012; 188: 703-713; and Japanese Patent No. 5186637) obtained by disrupting IL-5 gene by the insertion of a gene of a fluorescent protein Venus to exon 1 of the IL-5 gene, were used. On days 0, 7, and 14, 400 ng of recombinant IL-33 (rIL-33) (manufactured by R&D Systems, Inc.) was intraperitoneally administered to each mouse. On day 21, the lungs were resected from each mouse, and tissue sections were prepared and subjected to histological analysis.

Hematoxylin & eosin (H&E) staining and elastica van Gieson (EVG) staining were carried out using lung tissue sections fixed in 4% paraformaldehyde and then embedded in paraffin. The lung tissue sections were obtained by slicing the lung tissues into 4 μm using a microtome (manufactured by Sakura Finetek Japan Co., Ltd.) and preparing slides. The tissue sections were deparaffinized and then used in the staining. The tissues were observed using D-33E digital camera (manufactured by Olympus Corp.).

Immunofluorescent staining was carried out using lung tissue sections fixed in 4% paraformaldehyde and then embedded in OCT compound (manufactured by Sakura Finetek Japan Co., Ltd.). The lung tissue sections were obtained by slicing the lung tissues into 30 μm using a cryostat (manufactured by Leica Microsystems GmbH) and preparing slides. The tissue sections were blocked using TSA blocking reagent (manufactured by PerkinElmer Inc.), washed, and then reacted overnight with primary antibodies at 4° C. Then, the tissue sections were washed and then reacted with Alexa 488-, Alexa 568-, or Alexa 647-conjugated secondary antibodies (manufactured by Life Technologies Corp.).

The primary antibodies used were an anti-smooth muscle actin (SMA) antibody (1A4) (manufactured by Sigma-Aldrich Co., LLC), an anti-Siglec-F antibody (E50-2440) (manufactured by BD Biosciences), an anti-CD31 antibody (MEC13.3), an anti-CD3E antibody (145-2C11) (manufactured by BD Biosciences), and an anti-green fluorescent protein (GFP) polyclonal antibody (manufactured by Medical & Biological Laboratories Co., Ltd.). The slides thus reacted were loaded on Fluoromount (manufactured by Diagnostic Biosystems Inc.). Fluorescent images were observed using TSC SP5 confocal microscope/imaging system (manufactured by Leica Microsystems GmbH).

As a result, no change in lung tissue was observed in the wild-type mice and the IL-5$^{V/V}$ mice given phosphate buffer saline (PBS), whereas inflammatory reaction was observed in the lung tissues of the mice given rIL-33. Also, serious perivascular inflammatory reaction and vascular wall thickening were observed to be scattered in the wild-type mice given rIL-33, but were observed only slightly in the IL-5$^{V/V}$ mice given rIL-33. Immunocytes including eosinophils highly infiltrated into a perivascular inflammation site in the wild-type mice, but were rarely observed in the IL-5$^{V/V}$ mice.

A great majority of eosinophils accumulated in the periphery of smooth muscle cells in the wild-type and IL-5$^{+/V}$ mice, whereas the accumulation was completely inhibited in the IL-5$^{V/V}$ mice.

These results demonstrated that IL-5R+ eosinophils migrate and accumulate to the peripheral region of pulmonary blood vessels in a manner responsive to IL-33, thereby causing perivascular inflammation and vascular wall thickening.

Example 2

Involvement of IL-5-Producing Group 2 Innate Lymphoid Cell (ILC2) in IL-33-Responsive Eosinophil Accumulation Study was conducted on whether or not the number of (Venus-positive) CD3ε-negative ILC2 producing IL-5 would be increased in inflammatory tissues of the lungs ascribable to the long-term continuous administration of rIL-33. The lungs resected from each mouse were perfused with 5 mL of PBS and recovered. The whole pulmonary lobes were supplemented with 1 mL of RPMI1640 containing 10% fetal calf serum (FCS), 1 mg/mL collagenase (manufactured by F. Hoffmann-La Roche, Ltd.), and 100 g/mL DNase I (manufactured by Sigma-Aldrich Co. LLC) and chopped. After incubation at 37° C. for 1 hour in a $CO_2$ incubator, the chopped pulmonary lobes were passed through a 70 μm nylon mesh using a syringe. This cell suspension was used as a lung cell suspension.

The lung cell suspension was analyzed by flow cytometry (FCM) using various antibodies and FACSCanto II, FlowJo (manufactured by BD Biosciences). In the FCM, an anti-mouse B220 (RA3-6B2) antibody, an anti-CD11c antibody (HL3), an anti-CD19 antibody (1D3), an anti-CD45 antibody (30-F11), an anti-Gr1 antibody (RB6-8C5), an anti-FcεRI antibody (MAR-1), an anti-Mac-1 antibody (M1/70), and an anti-TER-119 antibody manufactured by eBioscience, an Affymetrix company were used. An anti-CD49b antibody (DX5) and an anti-NK1.1 antibody (PK136) manufactured by BioLegend were used. An anti-T1/ST2 antibody (DJ9) manufactured by MD Biosciences was used. The lung cell suspension was blocked using an anti-mouse FcγR antibody (2.4G2). Blood cell lineage (Lin) markers were stained using an anti-mouse B220, CD3ε, CD11c, CD19, CD49b, FcεRI, Gr1, Mac-1, NK1.1, and TER-119 antibody cocktail.

Plasma IL-5 concentrations were measured using mouse IL-5 ELISA kit (manufactured by Thermo Fisher Scientific Inc.).

Figure 2:
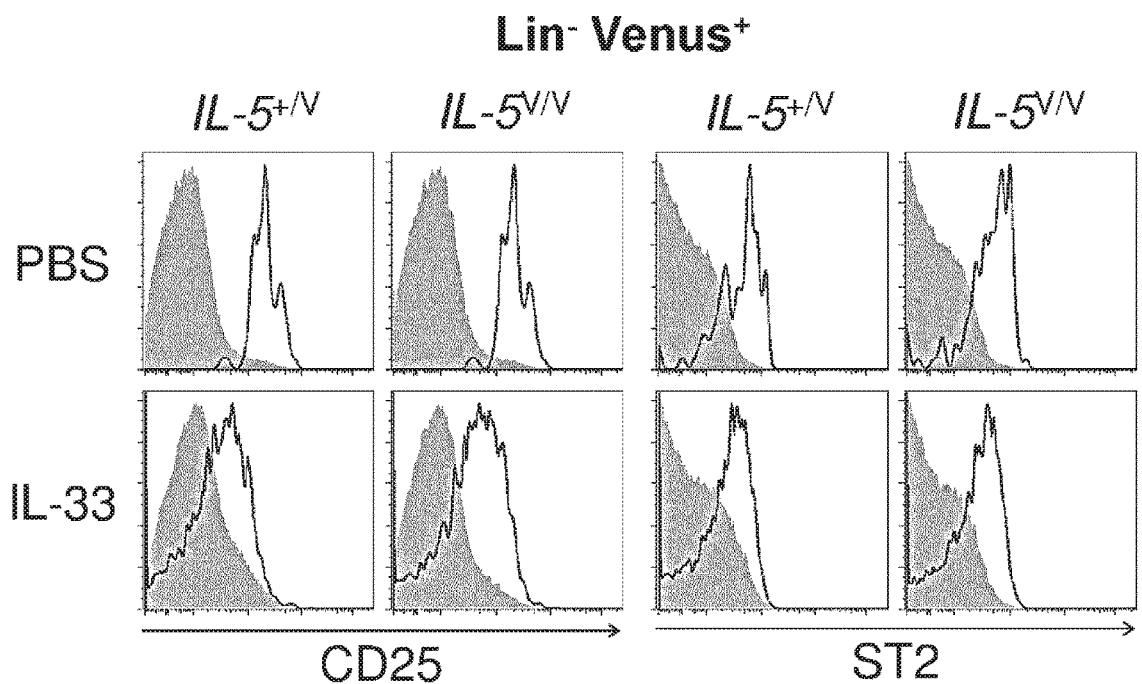
FIG. 2 shows CD25 expression and ST2 expression in the Lin-negative and Venus-positive (Lin⁻ Venus⁺) cells of IL-$5^{+/V}$ mice and IL-$5^{V/V}$ mice to which PBS or IL-33 was administered. The white histograms show Venus-positive cells, and the gray histograms show Venus-negative cells. In each graph, the ordinate depicts a cell number, and the abscissa depicts a CD25 or ST2 expression level.
Figure 3:
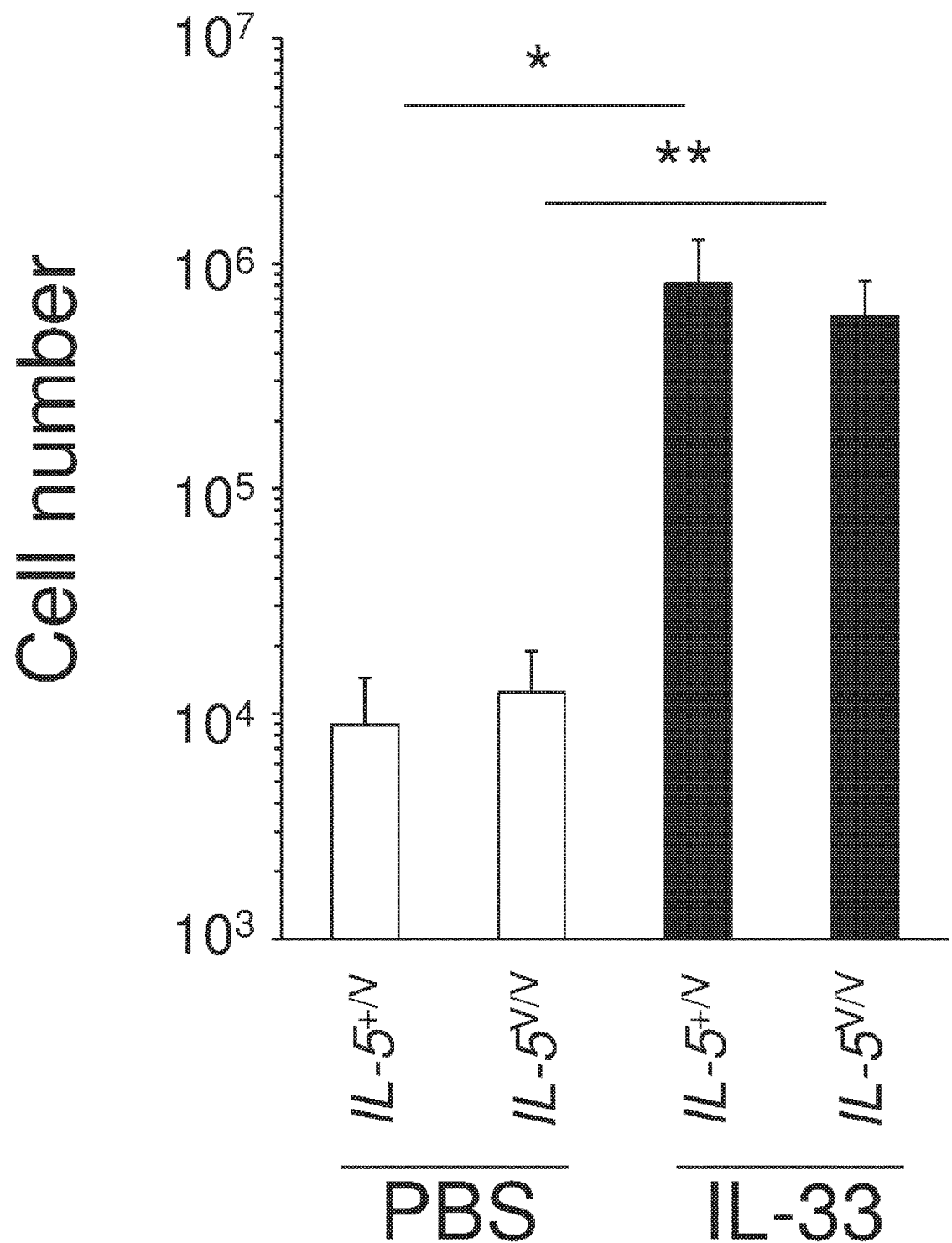
FIG. 3 shows the cell number of Lin Venus⁺ cells in IL-$5^{+/V}$ mice and IL-$5^{V/V}$ mice to which PBS or IL-33 was administered. The white graphs show a PBS administration group, and the black graphs show an IL-33 administration group.

As a result, the number of Venus-positive cells was increased in both of the IL-5$^{+/V}$ and IL-5$^{V/V}$ mice, demonstrating that 90% or more of Venus-positive cells are Lin-negative (FIG. 1). The Venus-positive cells expressed both of CD25 and ST2, demonstrating that these cells are Lin-negative, CD25-positive, ST2-positive, and Venus-positive group 2 innate lymphoid cells (ILC2) (FIG. 2). The number of Lin-negative, CD25-positive, ST2-positive, and Venus-positive ILC2 was increased 90-fold and 50-fold in the rIL-33 administration groups of the IL-5$^{+/V}$ mice and the IL-5$^{V/V}$ mice, respectively, compared with their control mice in the PBS administration groups (FIG. 3).

Figure 4:
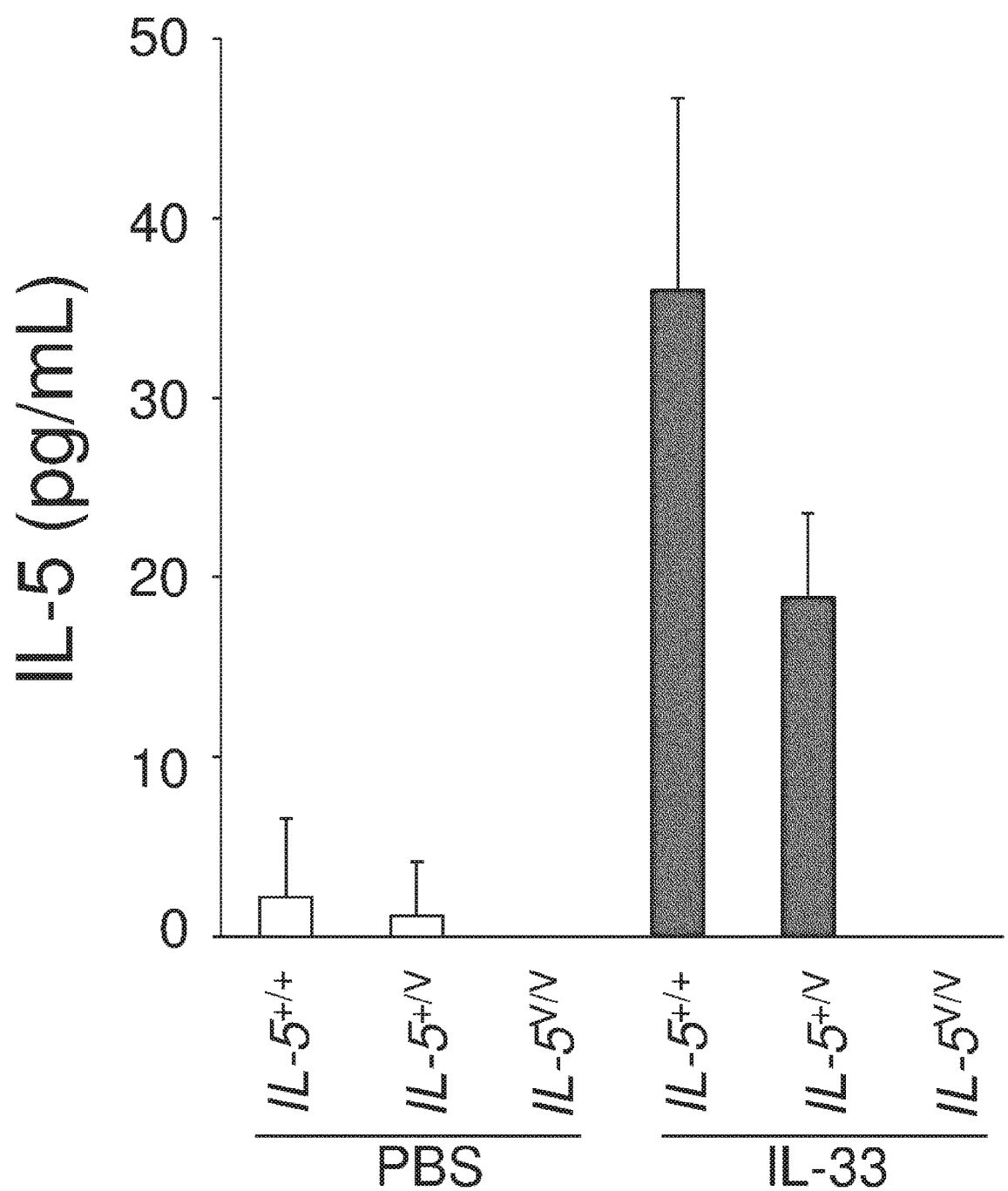
FIG. 4 shows a plasma IL-5 concentration (pg/mL) in IL-$5^{+/+}$ mice, IL-$5^{+/V}$ mice, and IL-$5^{V/V}$ mice to which PBS or IL-33 was administered. The white graphs show a PBS administration group, and the black graphs show an IL-33 administration group.
Figure 5:
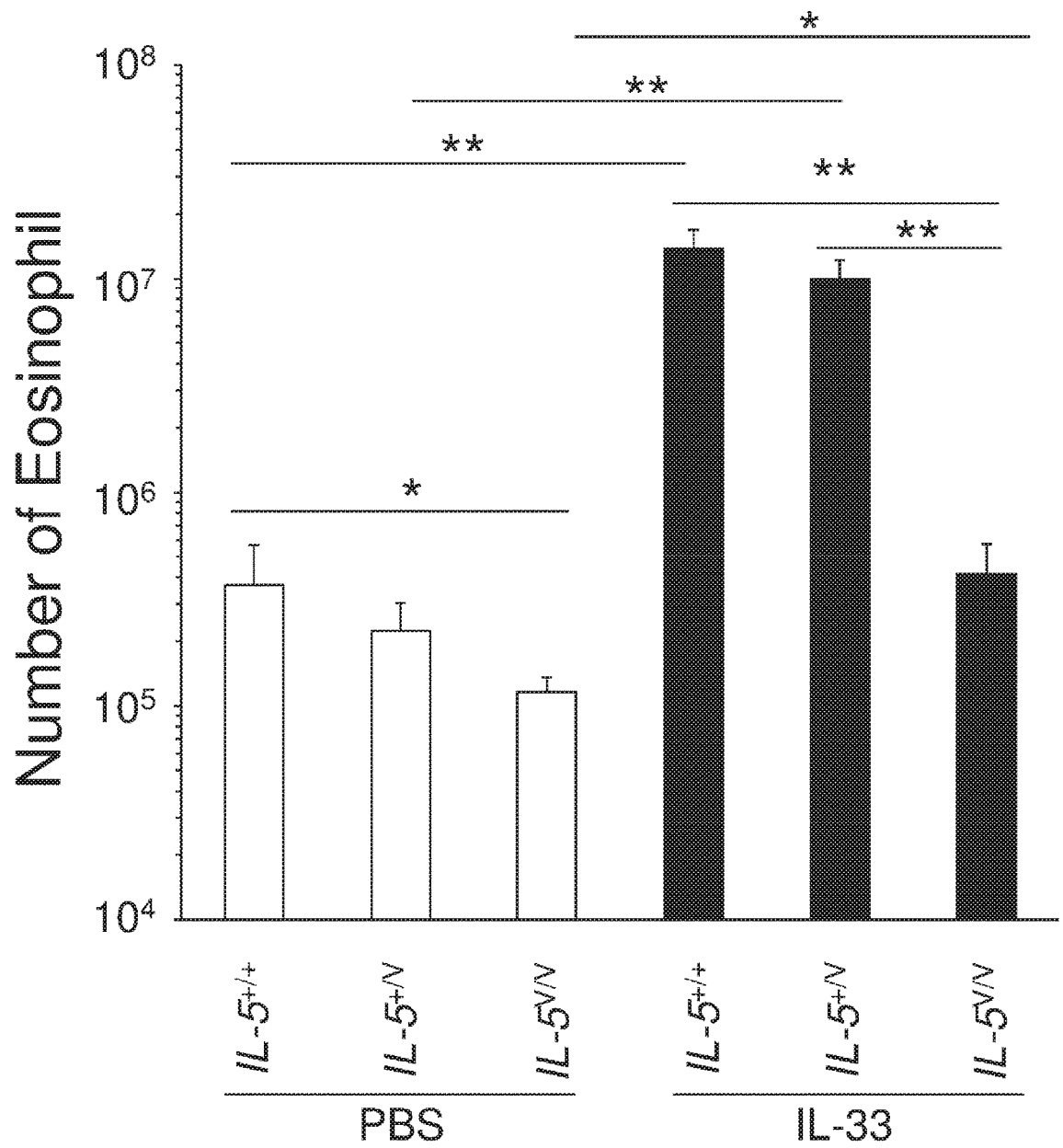
FIG. 5 shows the number of Siglec-F-positive eosinophils in IL-$5^{+/+}$ mice, IL-$5^{+/V}$ mice, and IL-$5^{V/V}$ mice to which PBS or IL-33 was administered. The white graphs show a PBS administration group, and the black graphs show an IL-33 administration group.

On the other hand, in the IL-5$^{+/+}$ mice and the IL-5$^{+/V}$ mice given rIL-33, marked increase in the production of IL-5 was observed, and an IL-5 concentration in peripheral blood was also increased (FIG. 4), whereas no increase in IL-5 level was observed in the IL-5$^{V/V}$ mice given rIL-33. The number of Siglec-F-positive eosinophils was increased approximately 50-fold in the IL-5$^{+/+}$ mice and the IL-5$^{+/V}$ mice given rIL-33 as compared with the IL-5$^{+/+}$ mice and the IL-5$^{V/V}$ mice given PBS, whereas increase in the number of eosinophils was rarely observed in the IL-5$^{V/V}$ mice given rIL-33 (FIG. 5).

These results demonstrated that Venus-positive ILC2 is involved in rIL-33-induced pulmonary vascular wall thickening and perivascular inflammation, and inflammation in the neighborhood of pulmonary blood vessels is caused by the migration induction, accumulation, and infiltration of ILC2-dependent eosinophils.

Example 3

Eosinophil-Dependent Serious Arterial Wall Thickening

Arterial wall thickening attributed to intimal thickening and medial thickening was significantly observed in IL-5$^{+/+}$ mice given rIL-33. Therefore, the degree of vascular wall thickening in IL-5$^{+/+}$ mice and IL-5$^{V/V}$ mice was quantitatively graded on the basis of the Heath-Edwards grading system. On days 0, 7, and 14, 400 ng of rIL-33 was administered to each mouse. On day 21, lung tissues were resected and subjected to pathological observation to conduct tissue classification on the basis of the Heath-Edwards grading system.

In this grading system, evaluation was carried out according to grade 1: medial thickening, grade 2: intimal thickening, grade 3: advanced intimal thickening and medial thickening, and grade 4; plexiform lesion in addition to advanced intimal thickening and medial thickening.

Figure 6:
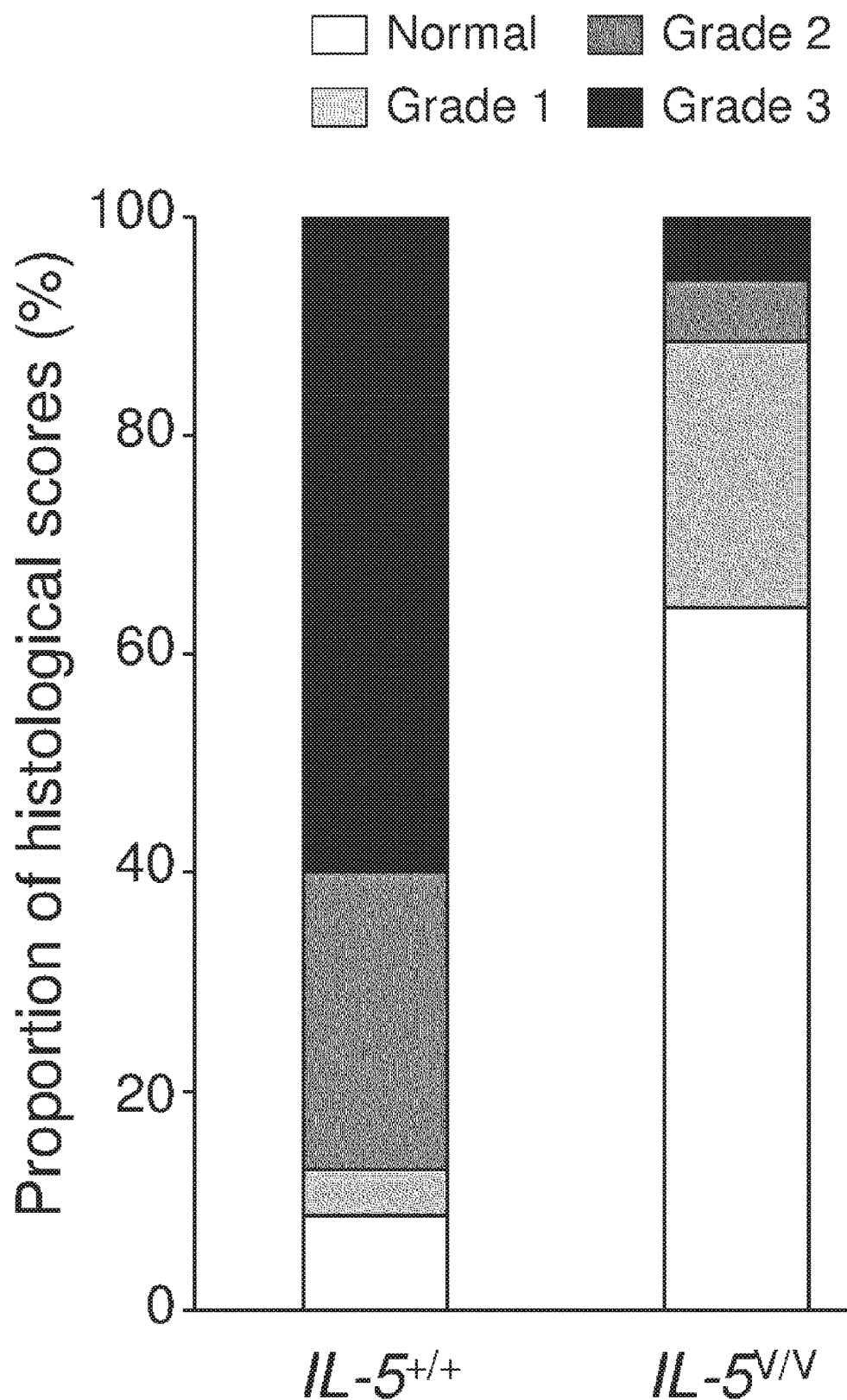
FIG. 6 shows histological scores based on the Heath-Edwards grading system of arterial wall thickening in IL-$5^{+/+}$ mice or IL-$5^{V/V}$ mice to which IL-33 was administered. This figure shows results of analyzing 70 arterial sites randomly selected from four mice each for groups.

As a result, in this classification, grade 1; 4%, grade 2; 27%, grade 3; 60%, and no change; 9% were found in the IL-5$^{+/+}$ mice, whereas grade 1; 24%, grade 2; 6%, grade 3; 6%, and no change; 64% were found in the IL-5$^{V/V}$ mice. Grade 4 was not confirmed in this test (FIG. 6).

From these results, rIL-33-dependent serious pulmonary vascular wall thickening was observed in the IL-5$^{+/+}$ mice. By contrast, in the IL-5$^{V/V}$ mice, pulmonary vascular wall thickening was evidently decreased, and low-grade vascular wall thickening was observed only slightly. These results demonstrated that IL-5-IL-5R signals are involved in pulmonary vascular wall thickening and the like and involved in increase in the severity of pulmonary hypertension. This suggested that pulmonary hypertension caused by pulmonary vascular wall thickening can be treated by inhibiting IL-5-IL-5R signals.

Example 4

Inhibitory Effect of Anti-IL-5 Neutralizing Antibody on Eosinophil-Dependent Serious Arterial Wall Thickening In an experimental system similar to that of Example 3, in order to confirm the inhibitory effect of an anti-IL-5 neutralizing antibody on intimal thickening and medial thickening, 100 μg of an anti-IL-5 rat monoclonal antibody (NC17) (Hitoshi et al., Int. Immunol., 1991; 3; 135-139) or a rat IgG control antibody (manufactured by Sigma-Aldrich Co., LLC) was intraperitoneally administered to each IL-5$^{+/+}$ mouse for 3 consecutive days (a total of 3 times) from two days before rIL-33 administration day. Then, on day 21, lung tissues were resected and subjected to pathological observation to conduct tissue classification on the basis of the Heath-Edwards grading system.

Figure 7:
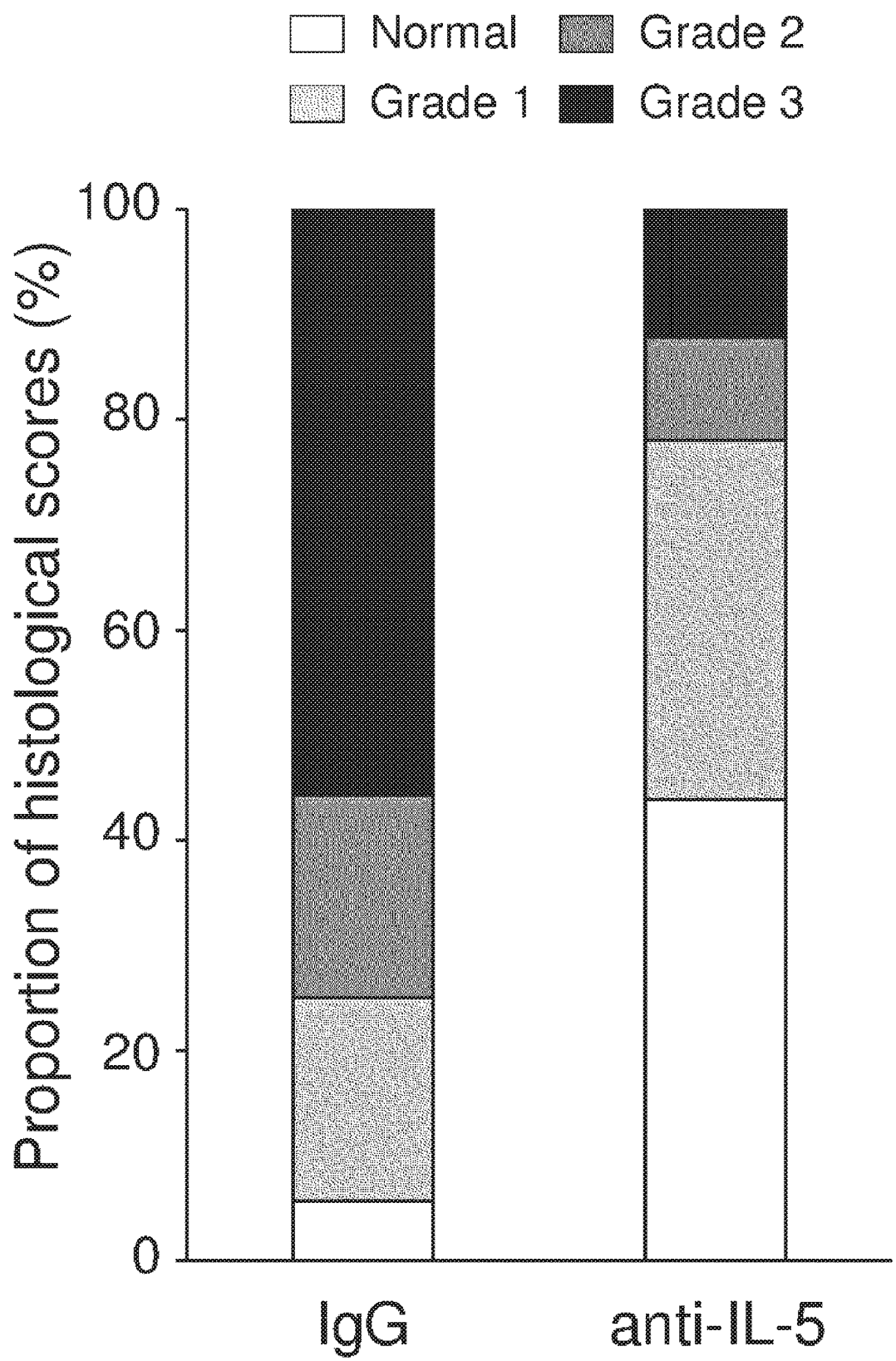
FIG. 7 shows histological scores of arterial wall thickening in IL-$5^{+/+}$ mice to which IL-33 was administered and then treated with an anti-mouse IL-5 rat monoclonal antibody or a control rat IgG antibody. This figure shows results of analyzing 82 arterial sites randomly selected from four mice each for groups.

As a result, serious pulmonary vascular wall thickening and inflammation were observed in the IL-5$^{+/+}$ mice of the control IgG antibody administration group, as in the case of administering rIL-33. By contrast, in the anti-IL-5 monoclonal antibody administration group, pulmonary vascular wall thickening and inflammatory tissues were evidently decreased, and the proportion of normal tissues or low-grade pulmonary vascular wall thickening was remarkably increased (FIG. 7), as observed in the IL-5$^{V/V}$ mice. These results demonstrated, as in Example 3, that IL-5-IL-5R signals are involved in serious thickening and inflammatory reaction in pulmonary blood vessels. These results further demonstrated that an antibody inhibiting IL-5-IL-5R signals significantly decreases inflammatory reaction in pulmonary blood vessels. This suggests that pulmonary vascular wall thickening and inflammatory reaction can be treated with any of an anti-IL-5 antibody, an anti-IL-5R antibody, and an IL-5R signal-specific inhibitory compound.

Example 5

Inhibitory Effect of Iloprost on Eosinophil-Dependent Serious Arterial Wall Thickening In an experimental system similar to that of Example 3, in order to confirm the effect of a prostacyclin derivative iloprost (manufactured by Cayman Chemical Company) serving as a therapeutic agent for pulmonary arterial hypertension, iloprost or PBS was intrabronchially administered to each IL-5$^{+/+}$ mouse on days 7 and 14 when rIL-33 was administered.

Figure 8:
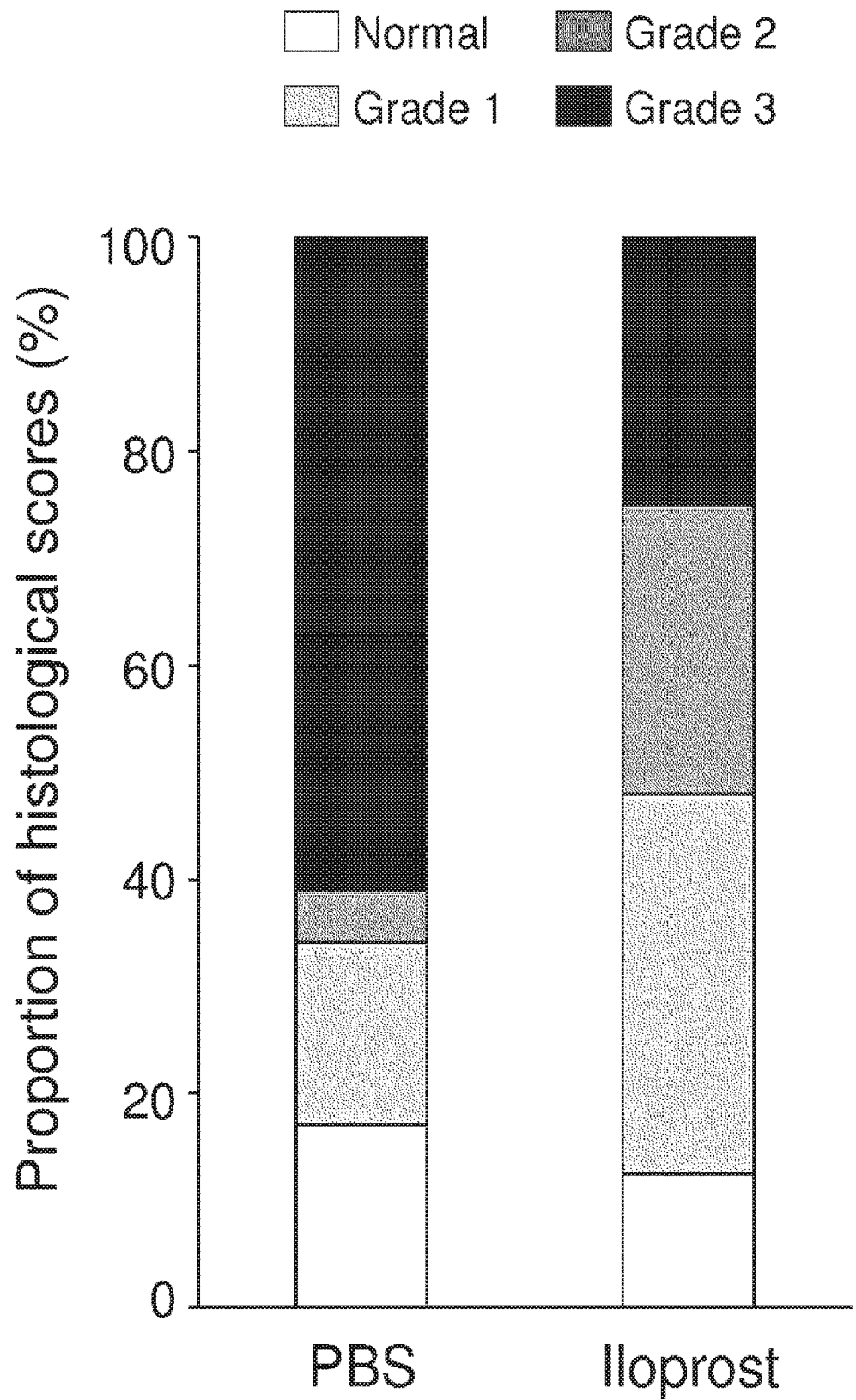
FIG. 8 shows histological scores of arterial wall thickening in IL-$5^{+/+}$ mice to which IL-33 was intraperitoneally administered and then intratracheally treated with PBS or iloprost. This figure shows results of analyzing 42 arterial sites randomly selected from four mice each for groups.

As a result, in the iloprost administration group compared with the PBS administration group, evident decrease in pulmonary vascular wall thickening was observed, and low-grade pulmonary vascular wall thickening was remarkably increased (FIG. 8). These results demonstrated that a prostacyclin derivative acts effectively on this rIL-33-induced pulmonary vascular wall thickening or inflammatory reaction.

Example 6

Pathological Relation of IL-33-Induced Arterial Wall Thickening to Human PAH

In order to carry out the vascular morphological analysis and right ventricular hypertrophy analysis of mice by long-term treatment with rIL-33, 400 ng of rIL-33 was intraperitoneally administered to each of IL-5$^{+/+}$ mice and IL-5$^{V/V}$ mice weekly for 11 weeks. After the completion of the administration, lung tissues were resected and subjected to pathological observation to conduct tissue classification on the basis of the Heath-Edwards grading system. In addition, the right ventricular free wall (RV) and the left ventricle+septum (LV+S) were resected, and their weights were measured to calculate (RV/LV+S) ratio.

(1) Histological Analysis

Figure 9:
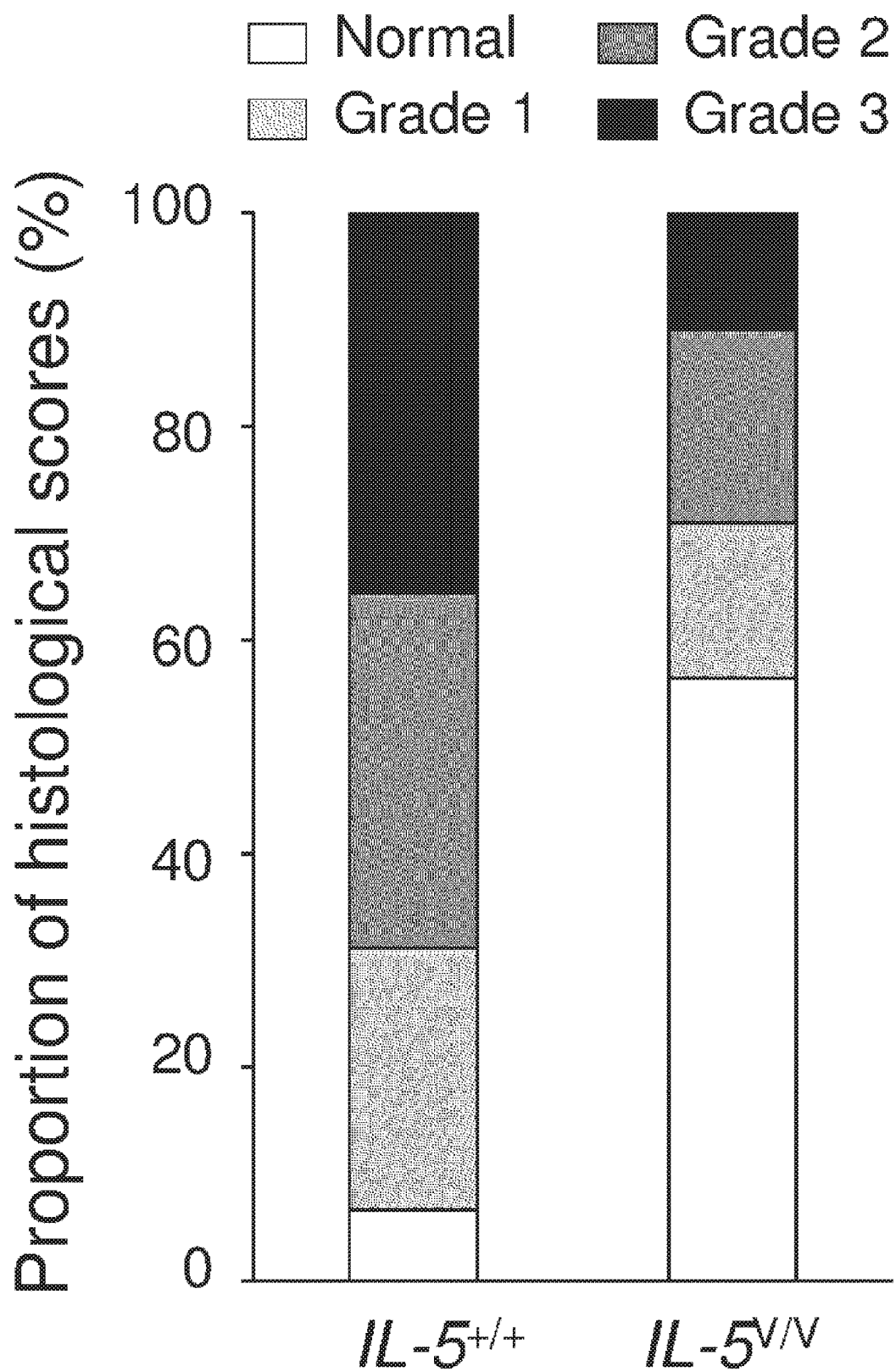
FIG. 9 shows histological scores of arterial wall thickening in IL-$5^{+/+}$ mice or IL-$5^{V/V}$ mice that underwent the long-term administration of IL-33 weekly for 11 weeks. This figure shows results of analyzing 45 or 55 arterial sites randomly selected from four mice each for groups.

As a result, serious pulmonary vascular wall thickening was observed in the IL-5$^{+/+}$ mice that underwent the long-term treatment with rIL-33, as in the mice given rIL-33 for 3 weeks shown in Example 3. By contrast, in the IL-5$^{V/V}$ mice, pulmonary vascular wall thickening was remarkably decreased, and normal tissues or tissues with low-grade pulmonary vascular wall thickening were found (FIG. 9). Lung tissues obtained from human pulmonary arterial hypertension (PAH) patients are at the final stage of the disease, and the infiltration and accumulation of eosinophils are rarely confirmed in such tissues. Surprisingly, this rIL-33 long-term administration mouse model exhibited pathology very similar to that of the PAH patient-derived tissues. In the IL-5$^{+/+}$ mice, eosinophil infiltration was remarkably hindered, and increase in the number of smooth muscle cells was observed. On the other hand, neither the infiltration of eosinophils nor increase in the number of smooth muscle cells was confirmed in the IL-5$^{V/V}$ mice, as in the mice given rIL-33 for 3 weeks.

Figure 10:
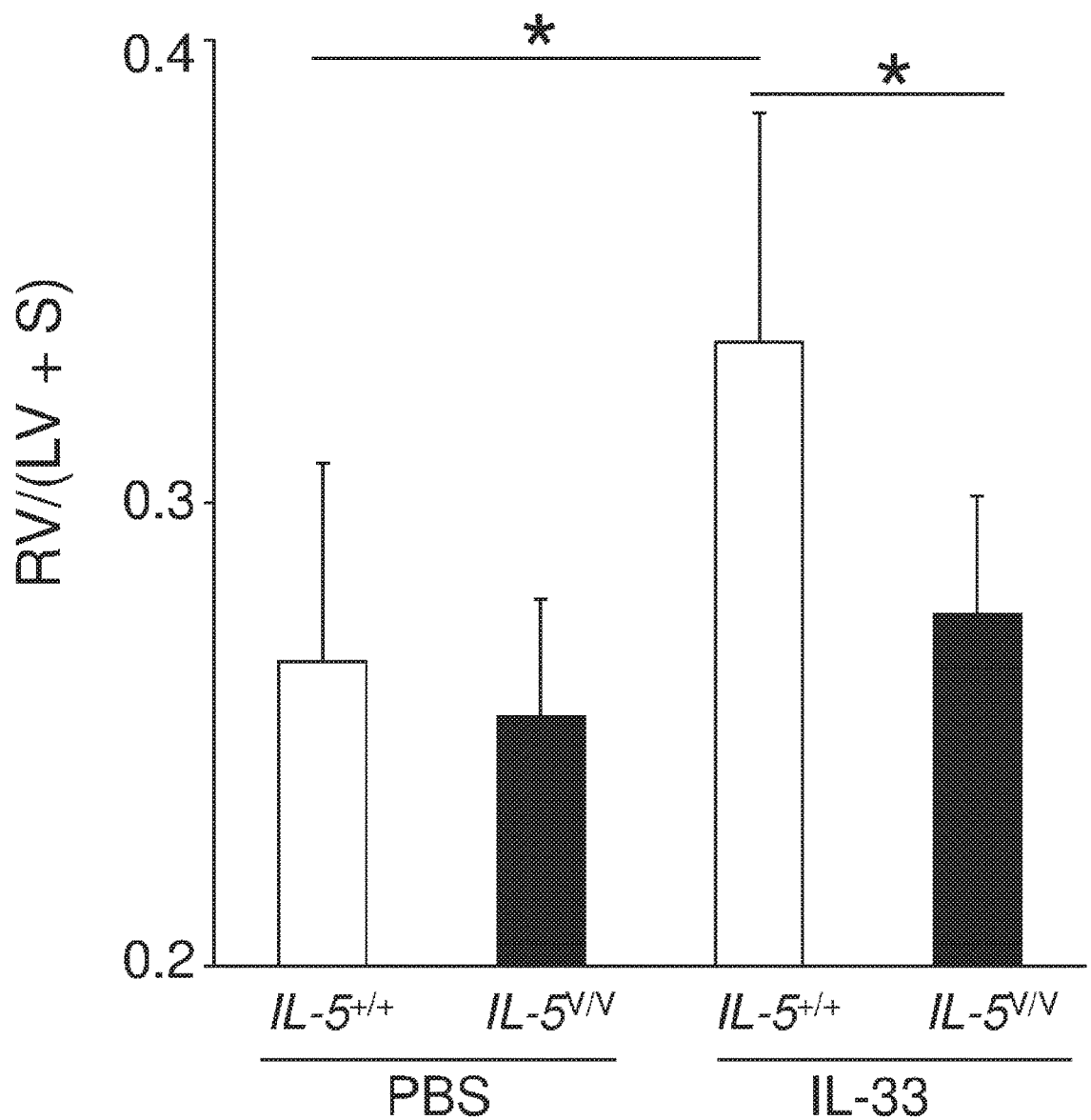
FIG. 10 shows the comparison of pulmonary hypertensive symptoms in IL-$5^{+/+}$ mice or IL-$5^{V/V}$ mice that underwent the long-term administration of IL-33 weekly for 11 weeks. The degree of the pulmonary hypertensive symptoms was indicated by RV/(LV+S) value. The ordinate depicts a RV/(LV+S) value, and the abscissa depicts each treated mice.

From the results of measuring ventricle weights, the (RV/LV+S) ratio was significantly increased in the IL-5$^{+/+}$ mice given rIL-33 as compared with the mice given PBS, whereas no increase in (RV/LV+S) ratio was found in the IL-5$^{V/V}$ mice given rIL-33 as compared with the mice given PBS (FIG. 10).

Meanwhile, histopathological analysis was re-conducted using tissues derived from 5 pulmonary hypertension patients. As a result, most of arteries were at an advanced stage of vascular wall thickening, and findings on perivascular inflammation were rarely observed. In two out of the 5 cases, the perivascular infiltration of eosinophils was observed, and moderate vascular wall thickening was observed according to the number of eosinophils.

These results suggest that rIL-33 long-term treatment mouse models reflect the histopathology of PAH patients and reflect chronic-phase inflammation in the periphery region of pulmonary arteries, pulmonary arterial wall thickening, and pulmonary vascular remodeling. The results of this long-term treatment also demonstrated that the IL-5-IL-5R signaling system is involved in the exacerbation and progression of a pathological condition of PAH.

(2) Plasma ST2 Marker Analysis

Figure 11:
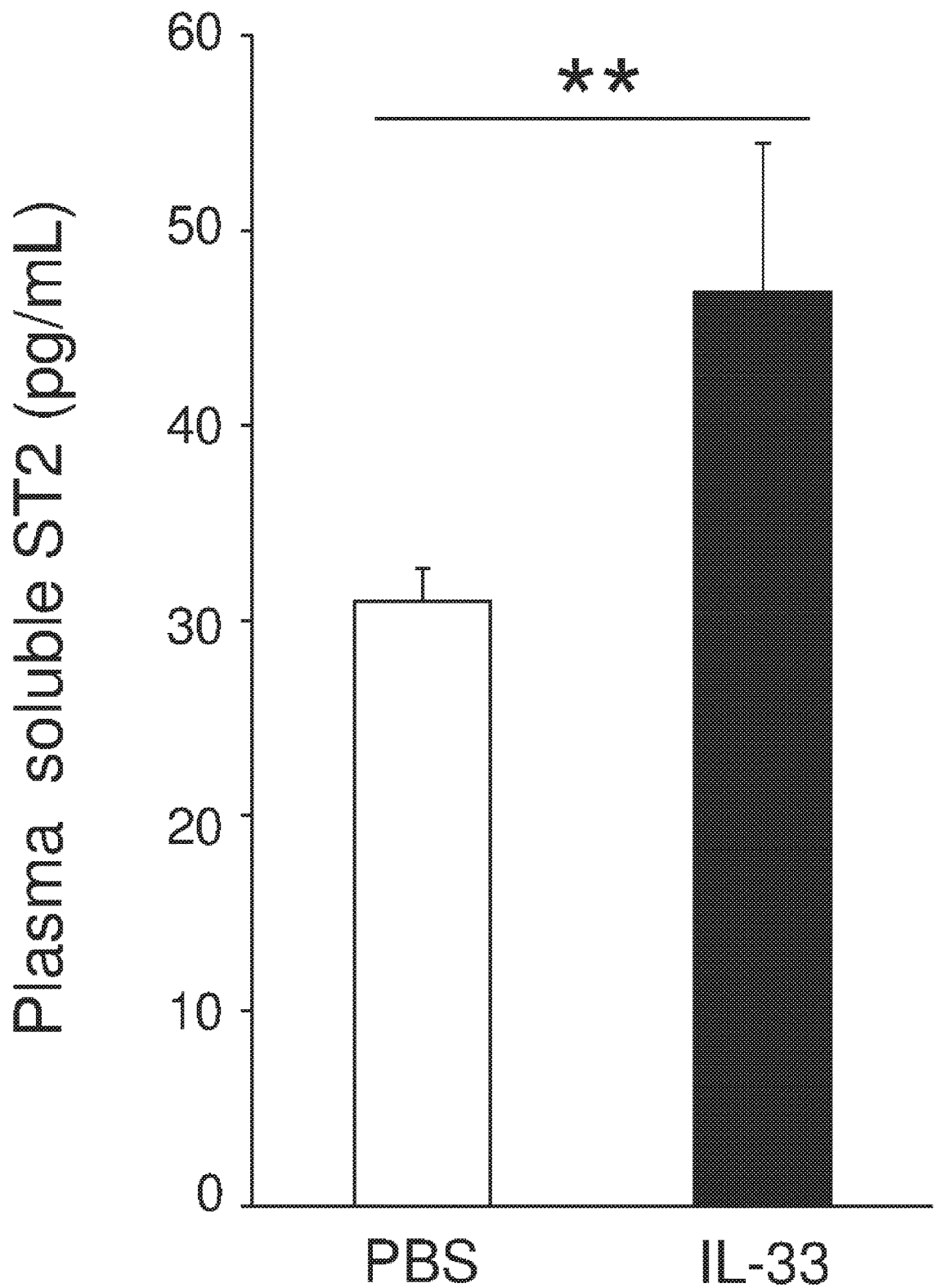
FIG. 11 shows the concentration of plasma soluble ST2 in IL-$5^{+/+}$ mice that underwent the long-term administration of IL-33 weekly for 11 weeks. The ordinate depicts a ST2 concentration (pg/mL), and the abscissa depicts the treatment of the mice.

The level of soluble ST2 is reportedly increased in the peripheral blood of PAH patients. Therefore, the plasma ST2 concentrations of the mice in this experimental model were measured. For the measurement, mouse ST2 ELISA kit (manufactured by R&D Systems, Inc.) was used. As a result, the ST2 concentration was significantly increased in the mice given rIL-33 (FIG. 11), demonstrating that this mouse model reflects the pathological conditions of human PAH patients.

These results demonstrated that ILC2-mediated eosinophil migration is caused in a manner responsive to IL-33 so that inflammatory reaction in the peripheral region of pulmonary blood vessels, pulmonary vascular wall thickening, and pulmonary vascular remodeling are caused in stages, thereby causing pulmonary hypertension from the acute phase to the chronic phase. This suggests that IL-5-IL-5R signals play an important role in this pathological mechanism of pulmonary hypertension, and an anti-IL-5R antibody capable of directly inhibiting and removing eosinophils expressing IL-5R is useful in the treatment of pulmonary hypertension.

Example 7

Obtainment of Gene Sequence of Anti-IL-5R Rat Monoclonal Antibody H7

Total RNA was extracted from a rat hybridoma H7 (Hitoshi et al., J. Immunol., 1990; 144; 4218-4225) using RNeasy Mini Kit (Qiagen N.V.), and 1st strand cDNA was synthesized using SMARTer RACE cDNA Amplification Kit (manufactured by Clontech Laboratories, Inc.). An antibody gene fragment was amplified by PCR using Universal Primer A Mix included in the kit, primers recognizing rat light chain and heavy chain constant regions (rat kappa re: SEQ ID NO: 11, rat gamma re: SEQ ID NO: 12), and PrimeSTAR Max DNA Polymerase (manufactured by Takara Bio Inc.). The PCR was performed by incubation at 96° C. for 2 min followed by 35 repetitive cycles each involving 98° C. for 10 sec, 55° C. for 15 sec, and 72° C. for 10 sec. The amplified gene fragment was separated on an agarose gel, excised from the gel using QIAquick Gel Extraction Kit (manufactured by Qiagen N.V.), and purified. The amplified antibody gene fragment was subcloned into pCR4 Blunt TOPO vector using Zero Blunt TOPO PCR Cloning Kit (manufactured by Life Technologies Corp.) and the antibody gene and amino acid sequences of the H7 antibody were determined by sequence analysis (using the primers M13F and M13R sequences). The obtained nucleotide sequences and amino acid sequences are shown in SEQ ID NOs: 13 to 18.

Example 8

Preparation of Various Recombinant Chimeric Antibodies of Anti-IL-5R Rat Monoclonal Antibody H7 for In Vitro Activity Evaluation (1) Subcloning into Antibody Expression Vector In order to conduct the activity evaluation of H7 recombinant chimeric antibodies, the constant regions of the rat monoclonal antibody H7 were recombined into human IgG1 constant regions, and human-type chimeric antibody without core-fucose (hereinafter, also referred to as a Potelligent-type antibody) was prepared and used. A human IgG1 (N297A)-type antibody deficient in N-linked sugar chain by use of a variant IgG1 sequence containing amino acid residue substitution at EU index N297A was used as a control lacking ADCC activity. A VL region or VH region gene was amplified by PCR (incubation at 96° C. for 2 min followed by 30 cycles each involving 98° C. for 10 sec, 55° C. for 5 sec, and 72° C. for 10 sec) using pCR4 Blunt TOPO vector as a template and primers designed for In-Fusion reaction (VL fw, VL re, VH fw, and VH re: SEQ ID NOs: 19 to 22), and excised from a gel and purified in the same way as in Example 7. Since there was the possibility that free Cys which was present in the proximal region of CDR3 of the H7 VL region, specifically, at position 87 from the N terminus, might influence physical properties, a VL region gene for a H7 (CS) altered form was prepared using primers mutated to replace this Cys with Ser (VL (CS) fw and VL (CS) re: SEQ ID NOs: 23 and 24). The following vectors were used for subcloning: pCI-neo'_hK vector (altered form of pCI vector manufactured by Promega Corp.), which was a vector having a gene insert of a human light chain constant region with a signal sequence, was cleaved with restriction enzymes XbaI and BsiWI (manufactured by New England Biolabs Inc. (NEB)), excised from a gel, purified, and used for the VL region. pCI-puro_hG1 (altered form of pCI vector manufactured by Promega Corp.) or pCI-puro hG1 (N297A) vector, which was a vector having a gene insert of a human IgG1 heavy chain constant region with a signal sequence, was cleaved with restriction enzymes FspAI (Thermo Fisher Scientific Inc.) and NheI (manufactured by New England Biolabs Inc. (NEB)), excised from a gel, and purified, and used for the VH region. The purified H7 VL or H7 (CS) VL fragment was mixed with the cleaved pCI-neo'_hK vector, and the In-Fusion reaction between the vector fragment and the antibody gene fragment was performed using In-Fusion HD Cloning Kit (manufactured by Clontech Laboratories, Inc.). The H7 VH fragment was subjected to In-Fusion reaction with the pCI-puro_hG1 or pCI-puro_hG1 (N297A)

vector. DH5α competent cells (manufactured by Takara Bio Inc.) were transformed with the solutions thus reacted to obtain colonies. Some colonies were cultured, and plasmids were extracted (PI-50, manufactured by Kurabo Industries Ltd.). A clone having inserts of the correct sequences was selected using a DNA sequencer (manufactured by Applied Biosystems Inc. (ABI)). The E. coli was scaled up and cultured, and plasmids were prepared using NucleoBond Xtra Midi EF (manufactured by Takara Bio Inc.).

(2) Transient Expression of Chimeric Antibody by Animal Cell

Various chimeric antibodies were transiently expressed using the prepared chimeric antibody expression vectors and FreeStyle MAX CHO Expression System Kit (manufactured by Life Technologies Corp.). For the expression of the Potelligent-type (Defucose, DF) antibody, α1,6-fucosyltransferase (FUT8)-knockout CHO cells (Fut8$_{-/-}$) (International Publication Nos. WO 2005/035586 and WO 02/31140) were acclimatized to FreeStyle CHO Expression Medium (manufactured by Life Technologies Corp.), and the resulting line was used as host cells. For the expression of the N297A-type antibody, CHO-S cells included in the kit were used. The method for plasmid transfer abided by the attached document, and the light chain expression vector and the heavy chain expression vector were mixed at a ratio of 1:2 and used in transfection. The cells thus transfected with the plasmids were cultured in 200 mL of a culture solution under conditions involving 37° C., 5% $CO_2$, and 125 rpm for 5 days. Then, the cell culture solution was centrifuged and passed through a 0.2 μm filter (manufactured by Thermo Fisher Scientific Inc.) to recover a culture supernatant. The combinations of the prepared chimeric antibodies, the host cells, and the plasmids used in transfection are shown in Table 1.

TABLE 1

Combinations of prepared antibodies, host cells used, and plasmids

| Name | Prepared chimeric antibody | Host | Plasmid for light chain expression | Plasmid for heavy chain expression |
|------|---------------------------|------|-----------------------------------|-----------------------------------|
| H7-1 | H7 hIgG1 (DF) | Fut8$^{-/-}$ | pCI-neo'_hK_H7-VL | pCI-puro_hG1_H7-VH |
| H7-2 | H7 (CS) hIgG1 (DF) | Fut8$^{-/-}$ | pCI-neo'_hK_H7 (CS)-VL | pCI-puro_hG1_H7-VH |
| H7-3 | H7 hIgG1 (N297A) | CHO—S | pCI-neo'_hK_H7-VL | pCI-puro_hG1 (N297A)_H7-VH |
| H7-4 | H7 (CS) hIgG1 (N297A) | CHO—S | pCI-neo'_hK_H7 (CS)-VL | pCI-puro_hG1 (N297A)_H7-VH |

(3) Small-Scale Purification of Antibody from Culture Supernatant

Each purified antibody was obtained from the culture supernatant by affinity purification using MabSelect SuRe (manufactured by GE Healthcare Japan Corp.). Specifically, a resin packed in a column was equilibrated with PBS. Then, the culture supernatant was added to the column, which was then washed twice with PBS and washed once each with wash buffer 1 (PBS with 1 M NaCl) and with wash buffer 2 (20 mM citric acid and 50 mM NaCl, pH 5.0), followed by the elution of the antibody using an elution buffer (20 mM citric acid and 50 mM NaCl, pH 3.4). The obtained antibody solution was neutralized by the addition of a neutralization buffer (1 M phosphoric acid-NaOH, pH 7.0) in a 1/10 amount, and the solvent in the antibody solution was replaced with PBS using NAP25 (manufactured by GE Healthcare Japan Corp.). The antibody solution thus buffer-replaced was concentrated by ultrafiltration using Amicon Ultra-4 Centrifugal Filter Units (manufactured by Merck Millipore). Absorbance $A_{280}$ was measured using Nanodrop (manufactured by Thermo Fisher Scientific Inc.). The concentration of the antibody solution was measured and adjusted.

Example 9

Preparation of H7 Recombinant Chimeric Antibody for In Vivo Activity Evaluation

Nucleotide sequences encoding the VH and VL of each H7 chimeric antibody or H7 (CS) chimeric antibody were inserted in tandem to appropriate positions of an appropriate antibody expression vector for animal cells (containing gene inserts of a human κ chain constant region, a human IgG1 chain constant region or an IgG1 (N297A) chain constant region) by use of In-Fusion Cloning. The nucleotide sequences encoding the expressed variable regions of the H7 chimeric light chain, the H7 (CS) chimeric light chain, the H7 chimeric IgG1 heavy chain, and the H7 chimeric IgG1 (N297A) heavy chain are shown in SEQ ID NOs: 25 to 28. The prepared antibody expression vector was transferred to CHO-K1 or CHO-K1 (Fut8) line by electroporation, and drug selection was performed to obtain cell lines stably expressing the chimeric antibodies corresponding to H7-1 to H7-4 of Table 1.

The obtained lines expressing various recombinant chimeric antibodies were each cultured at a scale of 400 mL for 10 days using BalanCD CHO GROWTH A+BalanCD CHO Feed 1 medium (manufactured by Irvine Scientific) to obtain a culture supernatant. After affinity purification using MabSelect SuRe column, a fraction containing a high monomer content was separated for the hIgG1-type antibody by cation-exchange chromatography using Fractogel SE Hicap (M) (manufactured by Merck Millipore), and the buffer was replaced with PBS using NAP25. Since the initial monomer content of the IgG1 (N297A)-type antibody was small, a monomer fraction was separated and obtained by gel filtration chromatography using Superdex 200 10/300GL (manufactured by GE Healthcare Japan Corp.). The obtained antibody solution was confirmed to be endotoxin-free using Limulus ES-II Test Wako (manufactured by Wako Pure Chemical Industries, Ltd.). Also, a core fucose-deficient anti-dinitrophenol (DNP) rat/human chimeric antibody KM8808, and an N-linked sugar chain-deficient anti-DNP rat/human chimeric antibody KM6161 containing N297A amino acid residue substitution were prepared as isotype control antibodies in the same way as above.

Example 10

Evaluation of Cell Responsiveness of H7 Recombinant Chimeric Antibody

The chimeric antibodies prepared in Example 8 were evaluated for their antigen binding activity using a mouse-derived cell line Y16 expressing IL-5R. The Y16 cells were washed with SM (staining medium containing 2% FCS, 0.05% $NaN_3$, and 1 mM EDTA in PBS). Then, Mouse BD Fc Block (manufactured by Becton, Dickinson and Company) was added thereto at a concentration of 5 μg/mL, and the mixture was left standing at 4° C. for 30 min. The cells were inoculated at a cell number of $1\times10^5$ cells/well to a 96-well U-bottom plate, and each chimeric antibody adjusted to a final concentration of 10000, 2500, 625, 156, 39, 10, 2.4, or 0.6 ng/mL was added thereto, followed by reaction at 4° C. for 60 min. The rat/human chimeric control antibodies used were rtDNP-1 hIgG1 (DF) antibody (KM8808) and rtDNP-1 hIgG1 (N297A) antibody (KM6161). The nucleotide sequences and amino acid sequences of the variable regions of each isotype control antibody are shown in SEQ ID NOs: 29 to 34. After washing of the cells with SM, Goat F(ab')$_2$ Anti-Human IgG PE (γ chain specific) (manufactured by Southern Biotech) diluted 500-fold with SM was added thereto, followed by reaction at 4° C. for 60 min. After washing of the cells with SM, the cells were resuspended in 50 μL of SM. Fluorescence intensity was measured by FCM (flow cytometer FACS Canto II (manufactured by Becton, Dickinson and Company)). The data was analyzed using FlowJo 7.65 (manufactured by Tomy Digital Biology Co., Ltd.) to calculate a Geomean value at each concentration.

Figure 12:
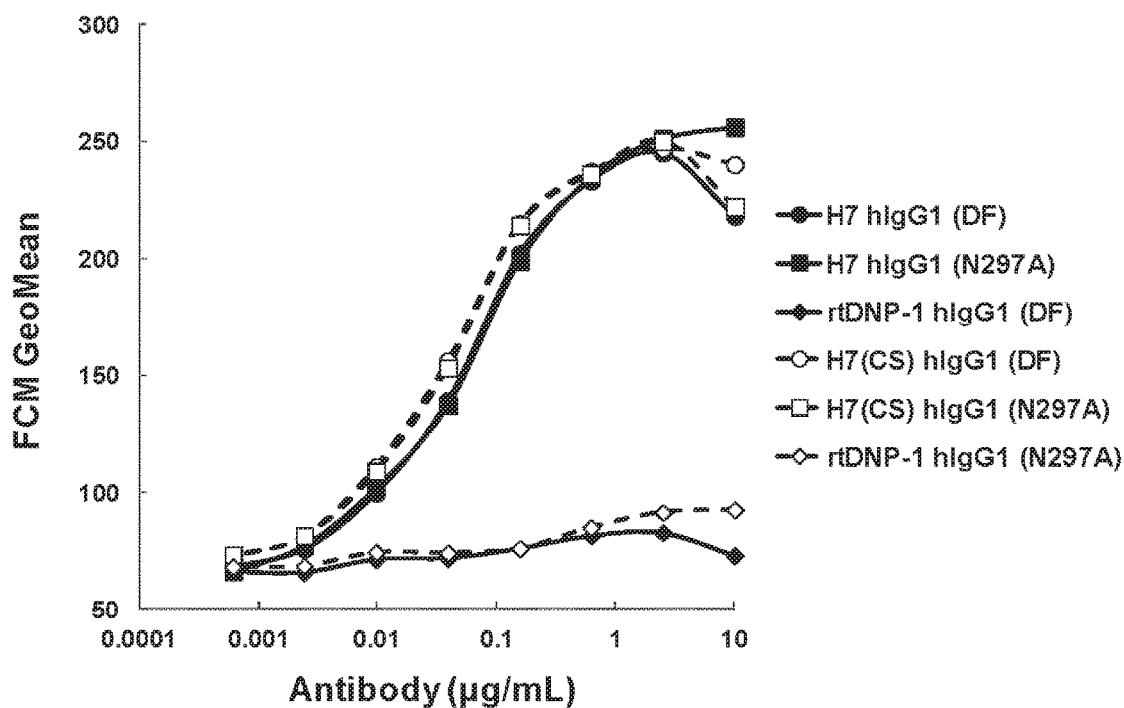
FIG. 12 shows the antigen-binding activity of chimeric antibodies. The ordinate depicts fluorescence intensity (Geomean value), and the abscissa depicts an antibody concentration.

The results are shown in FIG. 12. None of the anti-DNP antibodies bound to the cells, whereas the core fucose-deficient H7 chimeric antibody H7 hIgG1 (DF) (H7-1) and the N-linked sugar chain-deficient H7 chimeric antibody H7 hIgG1 (N297A) (H7-3) were confirmed to react equivalently with the mouse IL-5Rα-expressing cell Y16. The same held true for the Cys-substituted H7 (CS) altered forms of the H7 chimeric antibody (H7-2 and H7-4) When H7-1 and H7-2 were compared, the tendency of a slight rise in binding ability was found in the Cys substitution variant H7-2.

Example 11

Evaluation of Reactivity of H7 Recombinant Chimeric Antibody with Mouse FcγR

The various H7 chimeric antibodies prepared in Example 8 and the parent antibody H7 rat IgG2a-type antibody were evaluated for their affinity for mouse FcγR using Biacore T-200 (manufactured by GE Healthcare Japan Corp.). An anti-tetra His mouse antibody (manufactured by Qiagen N.V.) was immobilized with 8000 RU as a guideline onto CM5 sensor chip using an amine coupling kit (all manufactured by GE Healthcare Japan Corp.). The coupling buffer used was 10 mM sodium acetate (pH 4.5). His tag-fused mouse FcγRI, IIb, III, and IV proteins (all manufactured by R&D Systems, Inc.) each dissolved at 2 μg/mL in HBS-EP (+) were captured as ligands at 2 μL/min for 30 sec. Then, each antibody serially diluted into concentrations of 80, 40, 20, 10, 5, 2.5, 1.25, and 0.625 g/mL was added thereto as an analyte by the multicycle method. The flow rate was 5 μL/min, and the contact time and the dissociation time were both set to a condition of 240 sec. The analysis was carried out using Biacore T200 Evaluation software on the Steady State Affinity mode. The results are shown in Table 2. A rise in binding activity against FcγRI and FcγRIV involved in in vivo mouse effector activity was observed by the alteration of the H7 constant region from rat IgG2a type to hIgG1 type.

TABLE 2

Affinity of H7 antibodies differing in constant region for mouse FcγR

| | Affinity $K_D$ [nM] mAb | | |
|---|---|---|---|
| FcγR | H7 hIgG1 (DF) (H7-1) | H7 hIgG1 (N297A) (H7-3) | H7 ratIgG2a |
| FcγRI | 137 | very weak | very weak |
| FcγRIIb | no binding | no binding | no binding |
| FcγRIII | no binding | no binding | no binding |
| FcγRIV | 89.5 | no binding | very weak |

Example 12

Evaluation of ADCC Activity of H7 Recombinant Chimeric Antibody

The H7 recombinant chimeric antibodies prepared in Example 8 were evaluated for their ADCC activity against Y16 cells using frozen human peripheral blood mononuclear cells (PBMCs) (manufactured by AllCells) as effector cells. The frozen human PBMCs were shake-cultured (37° C., 5% $CO_2$, overnight) in RPMI1640 medium containing 5% FBS. The Y16 cells (target cells) and the human PBMCs (effector cells) were washed with ADCC assay medium (RPIM1640 containing 5% dialyzed FBS) and adjusted to cell densities of $2\times10^5$ cells/mL and $3\times10^6$ cells/mL, respectively. The cells were washed twice with a medium and then suspended into cell densities of $4\times10^5$ cells/mL. Each chimeric antibody adjusted to a final concentration of 0.0001, 0.001, 0.01, 0.1, 1, 10, 100, or 1000 ng/mL, the target cells ($2\times10^4$ cells/well), and the effector cells ($5\times10^5$ cells/well) were added in this order at 50 μL/well to a 96-well U-bottom plate. The control antibodies used were the rtDNP-1 hIgG1 (DF) antibody (KM8808) and the rtDNP-1 hIgG1 (N297A) antibody (KM6161) of Example 10 adjusted to a final concentration of 1000 ng/mL. The plate was centrifuged (500 rpm, 5 min) and then left standing in an incubator (37° C., 5% $CO_2$, 4 hrs). The plate was centrifuged (1500 rpm, 5 min) to recover a supernatant at 50 μL/well into a 96-well Flat-bottom plate (manufactured by Sumitomo Bakelite Co., Ltd.). Lactate dehydrogenase (LDH) activity in the supernatant was detected using CytoTox 96 Non-Radioactive Cytotoxicity Assay (manufactured by Promega Corp.). Absorbance at 490 nm was measured using a plate reader SPECTRA MAX 340 PC384 (manufactured by Molecular Devices, LLC). The ADCC activity (%) was calculated according to the following equation using background-corrected measurement values.

Cytotoxicity=[[Absorbance of the sample]–[Absorbance derived from spontaneous release from the target cells and the effector cells]]/[[Absorbance derived from total release from the target cells]–[Absorbance derived from spontaneous release from the target cells]]

Figure 13:
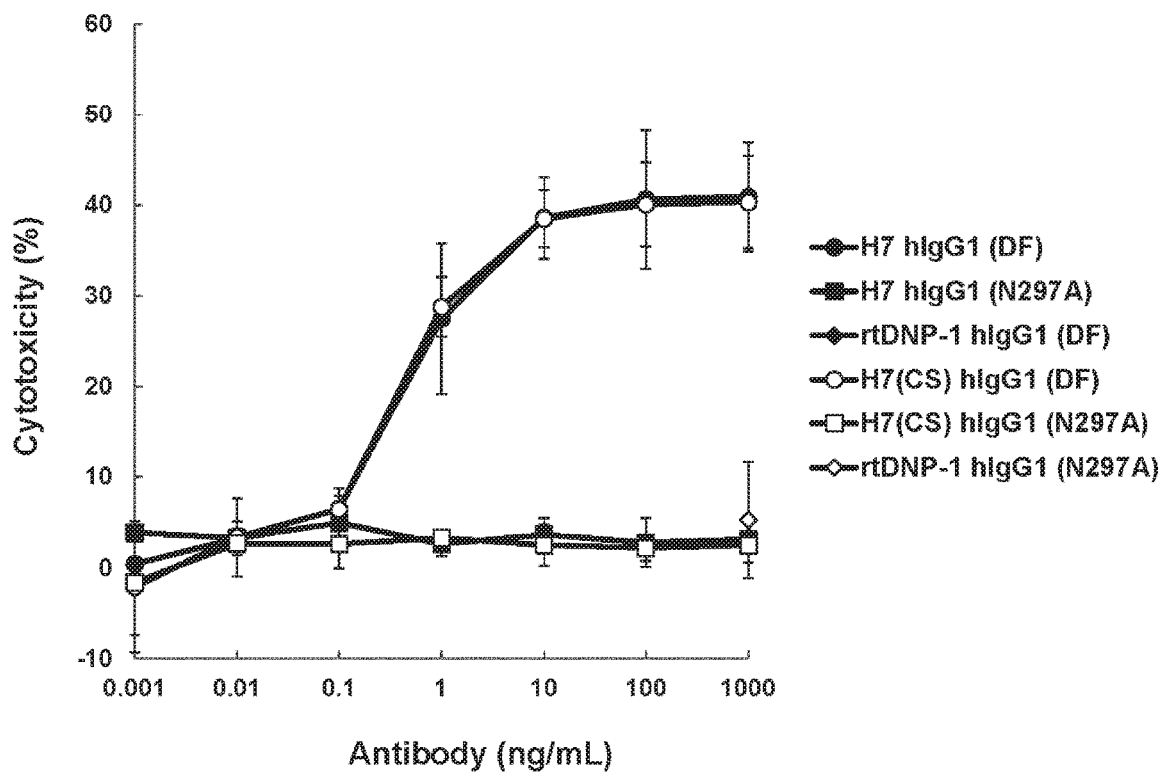
FIG. 13 shows the ADCC activity of chimeric antibodies against Y16 cells. The ordinate depicts ADCC activity (%), and the abscissa depicts an antibody concentration.

The results are shown in FIG. 13. The core fucose-deficient H7 recombinant chimeric antibodies H7 hIgG1 (DF) (H7-1) and H7 (CS) hIgG1 (DF) (H7-2) exhibited antibody concentration-dependent ADCC activity. On the other hand, none of the N-linked sugar chain-deficient H7 recombinant chimeric antibodies H7 hIgG1 (N297A) (H7-3) and H7 (CS) hIgG1 (N297A) (H7-4) and the anti-DNP antibodies KM8808 and KM6161 exhibited ADCC activity. These results demonstrated that no large difference in biological activity is founded between a H7 recombinant antibody and an antibody H7 (CS) containing Cys substitution, and a H7 recombinant chimeric antibody deficient in N-linked sugar chain lacks effector activity.

Example 13

Validation of IL-5 Signal-Inhibiting Function of Recombinant Chimeric Anti-IL-5Rα Chain Antibody Whether or not the various recombinant chimeric antibodies prepared in Example 8 would have the function of inhibiting IL-5 signals was studied by using Y16 growth inhibition as an index. $2 \times 10^3$ Y16 cells were cultured for 24 hours in the presence or absence of rIL-5 (5 units/mL) after addition of the Cys substitution-containing core fucose-unlinked H7 recombinant chimeric antibody H7 (CS) hIgG1 (DF) (H7-2), the N-linked sugar chain-deficient H7 recombinant chimeric antibody H7 (CS) hIgG1 (N297A) (H7-4), and the anti-DNP antibodies KM8808 and KM6161 at a concentration of 0.01, 0.1, 1, or 10 μg/mL. 24 hours later, these antibodies were evaluated for their ability to inhibit growth using Premix WST-1 Cell Proliferation Assay System (manufactured by Takara Bio Inc.). The culture time after addition of the reagent of the cell growth assay kit was set to 1 hour.

Figure 14:
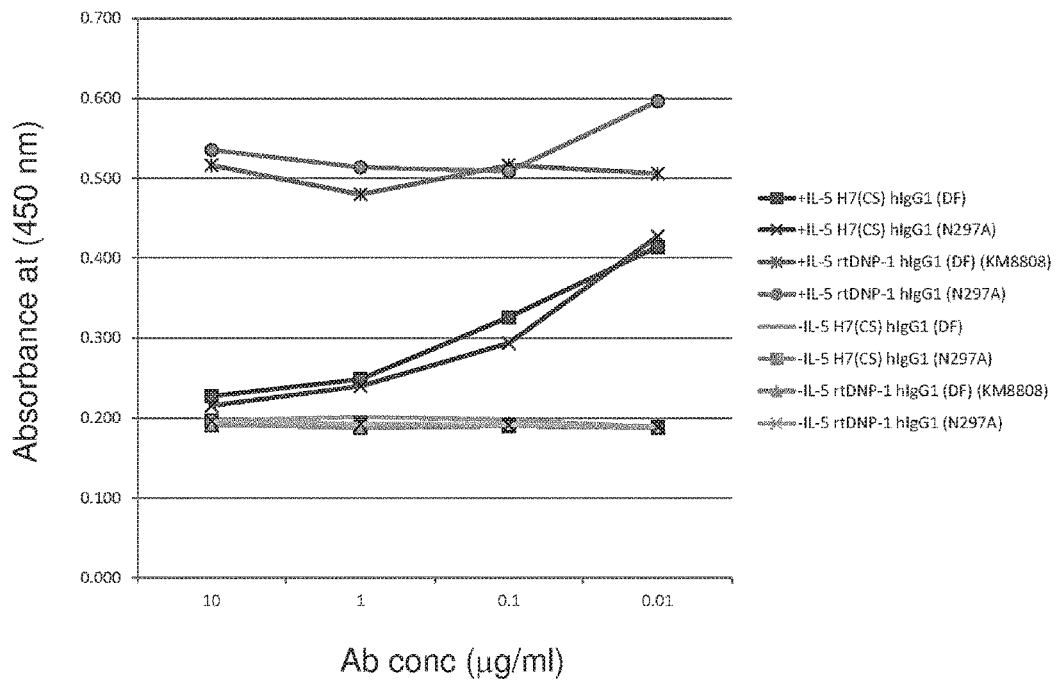
FIG. 14 shows the ability of chimeric anti-IL-5Rα chain antibodies to inhibit the growth of Y16 cells (IL-5 signal-inhibiting function). The ordinate depicts absorbance at 450 nm, and the abscissa depicts an antibody concentration.

As a result, the H7 (CS) hIgG1 (DF) (H7-2) antibody and the H7 (CS) hIgG1 (N297A) (H7-4) antibody inhibited the growth of the Y16 cells in an antibody concentration-dependent manner (FIG. 14). Growth inhibition by the isotype control rtDNP-1 hIgG1 (DF) antibody (KM8808) and rtDNP-1 hIgG1 (N297A) antibody (KM6161) was not observed. Also, Y16 growth was not observed in any of the experimental groups in the absence of rIL-5. From these results, the anti-IL-5Rα chain H7 recombinant chimeric antibodies prepared this time were confirmed to have the function of inhibiting IL-5 signals. Also, H7-2 and H7-4 had equivalent inhibiting ability.

Example 14

Figure 15:
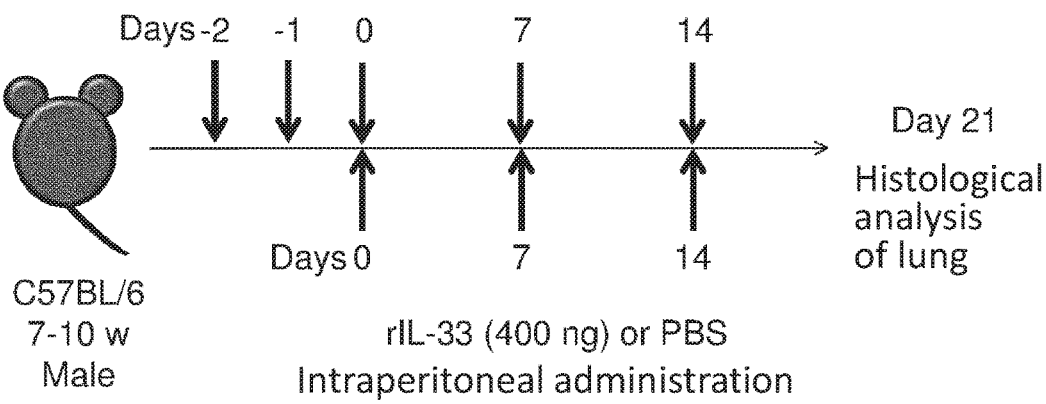
FIG. 15 shows an experimental scheme of the inhibitory effect of an anti-IL-5 antibody or an anti-IL-5R antibody on IL-33-induced vascular wall thickening (Example 14).

Validation of inhibitory effects of anti-IL-5Rα chain H7 recombinant chimeric antibody and anti-IL-5 antibody on IL-33-induced vascular wall thickening In an experimental system similar to that of Example 3, in order to confirm the inhibitory effects of anti-IL-5R antibodies and anti-IL-5 neutralizing antibodies on vascular wall thickening, 100 μg of the H7 (CS) hIgG1 (DF) (H7-2) antibody, the H7 (CS) hIgG1 (N297A) (H7-4) antibody, an anti-IL-5 antibody (ligand-neutralizing antibody, clone name: TRFK5), the anti-DNP antibody KM8808, the anti-DNP antibody KM6161, or rat IgG (clone name: HRPN) was intraperitoneally administered to each IL-5$^{+/+}$ mouse a total of five times (3 consecutive days (three times) from two days before the first rIL-33 administration day (day 0), once on the second rIL-33 administration day (day 7), and once on the third rIL-33 administration day (day 14)) (FIG. 15). Then, on day 21, lung tissues were resected and evaluated by FCM and immunofluorescent staining.

In the FCM, $1 \times 10^6$ cells in the lung cell suspension were stained with a PE-Cy7-conjugated anti-CD45 antibody (30-F11), an APC-conjugated anti-Gr1 antibody (RB6-8C5), and a PE-conjugated anti-Siglec-F antibody (E50-2440) (all manufactured by BD Biosciences). CD45-positive, Gr1-negative, and Siglec-F-positive cells were regarded as eosinophils, and the influence of antibody administration was observed.

In the immunofluorescent staining, the tissues were sliced into 30 μm, and slides were prepared and then stained with an Alexa 488-conjugated anti-SMA antibody (1A4) (manufactured by Abcam plc) and an Alexa 647-conjugated anti-Siglec-F antibody (E50-2440). The nuclei of the cells were stained with Hoechst 33342 (manufactured by Life Technologies Corp.). Here, the degree of the growth of SMA-positive cells (primary media-constituting cells) was observed.

Figure 16:
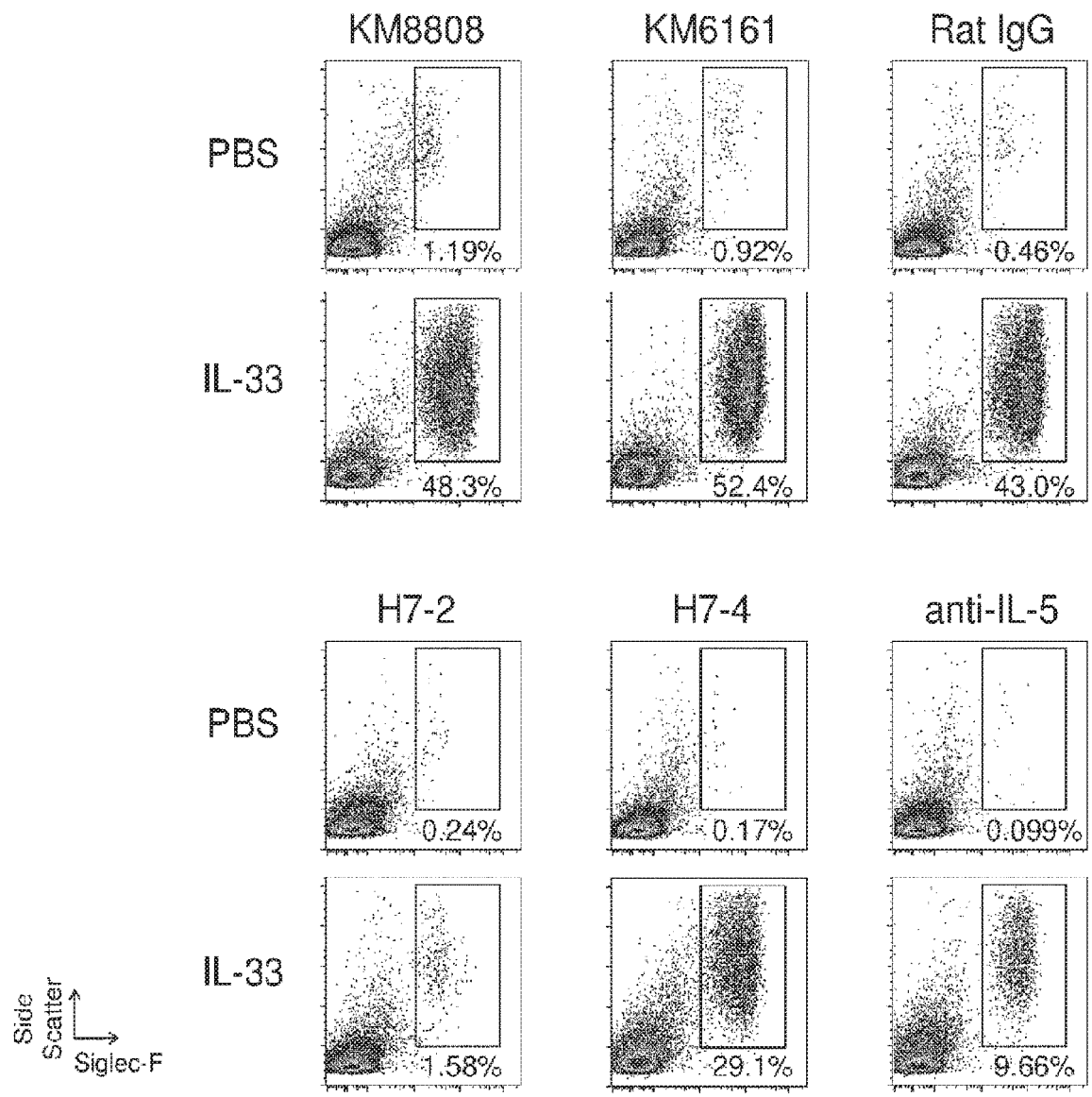
FIG. 16 shows results of evaluating the inhibitory effects of H7-2, H7-4, an anti-IL-5 antibody, KM8808, KM6161, and rat IgG on IL-33-induced vascular wall thickening by the FCM method (IL-33: in the presence of IL-33, PBS: in the absence of IL-33).

In the experiment results of the FCM, increase in the number of eosinophils was inhibited almost completely by the H7-2 antibody, inhibited by the H7-4 antibody at a degree poorer than that of H7-2, and inhibited by the anti-IL-5 antibody more effectively than H7-4, albeit inferior to H7-2 (FIG. 16). On the other hand, IL-33-induced increase in the number of eosinophils was not inhibited by any of the negative control antibodies (KM8808, KM6161, and rat IgG antibodies). The abundance ratio (%) of eosinophils in the presence or absence of IL-33 is shown in Table 3 as to each antibody.

TABLE 3

| Experimental results of FCM | | | | | |
|---|---|---|---|---|---|
| | KM8808 | KM6161 | Rat IgG | H7-2 | H7-4 | Anti-IL-5 antibody |
| In presence of IL-33 | 48.3% | 52.4 | 43.0 | 1.58 | 29.1 | 9.66 |
| In absence of IL-33 (PBS) | 1.19 | 0.92 | 0.46 | 0.24 | 0.17 | 0.099 |

In the experimental results of the immunofluorescent staining, vascular wall thickening was inhibited most strongly by the H7-2 antibody and inhibited by the H7-4 antibody and the anti-IL-5 antibody at a degree poorer than that of H7-2. On the other hand, the inhibition of IL-33-induced vascular wall thickening was not observed in any of the control antibodies (KM8808, KM6161, and rat IgG antibodies).

From these results, the antibody having ADCC activity (H7-2) was found to be superior in eosinophil growth-inhibiting function to the antibody that lost its ADCC function by lack of N-linked sugar chain (H7-4), or the anti-IL-5 antibody. These results also demonstrated that the H7-2 antibody therefore contributes to the more effective inhibition of vascular wall thickening. Since H7-2 and H7-4 had the equivalent ability to recognize the antigen and ability to inhibit IL-5 signals, it is concluded that the results obtained here are due to the presence or absence of ADCC. Also, the H7-2 antibody having ADCC activity exhibited a vascular wall thickening inhibitory effect superior to H7-4 or the IL-5 ligand-neutralizing antibody.

All publications, patents, and patent applications cited herein are incorporated herein by reference in their entirety.

INDUSTRIAL APPLICABILITY

The present invention is useful for a therapeutic agent and a therapeutic method for pulmonary hypertension.

All publications, patents, and patent applications cited herein are incorporated herein by reference in their entirety.

Free Text for Sequence Listing
SEQ ID NO: 1: HCDR1
SEQ ID NO: 2: HCDR2
SEQ ID NO: 3: HCDR3
SEQ ID NO: 4: LCDR1
SEQ ID NO: 5: LCDR2
SEQ ID NO: 6: LCDR3

SEQ ID NO: 7: VH
SEQ ID NO: 8: VL
SEQ ID NO: 9: Benralizumab heavy chain
SEQ ID NO: 10: Benralizumab light chain
SEQ ID NO: 11: Rat kappa re
SEQ ID NO: 12: Rat gamma re
SEQ ID NO: 13: Nucleotide sequence of an H7 antibody light chain variable region with a signal sequence
SEQ ID NO: 14: Amino acid sequence of the H7 antibody light chain variable region with a signal sequence
SEQ ID NO: 15: Amino acid sequence of the H7 antibody light chain variable region without the signal sequence
SEQ ID NO: 16: Nucleotide sequence of an H7 antibody heavy chain variable region with a signal sequence
SEQ ID NO: 17: Amino acid sequence of the H7 antibody heavy chain variable region with a signal sequence
SEQ ID NO: 18: Amino acid sequence of the H7 antibody heavy chain variable region without the signal sequence
SEQ ID NO: 19: VL fw
SEQ ID NO: 20: VL re
SEQ ID NO: 21: VH fw
SEQ ID NO: 22: VH re
SEQ ID NO: 23: VL (CS) fw
SEQ ID NO: 24: VL (CS) re
SEQ ID NO: 25: Nucleotide sequence of a recombinantly expressed H7 antibody light chain variable region
SEQ ID NO: 26: Nucleotide sequence of a recombinantly expressed H7 (CS) antibody light chain variable region
SEQ ID NO: 27: Nucleotide sequence of a recombinantly expressed H7 or H7 (CS) hIgG1 antibody heavy chain variable region
SEQ ID NO: 28: Nucleotide sequence of a recombinantly expressed H7 or H7 (CS) hIgG1 (N297A) antibody heavy chain variable region
SEQ ID NO: 29: Nucleotide sequence of the rtDNP-1 antibody light chain variable region with a signal sequence
SEQ ID NO: 30: Amino acid sequence of the rtDNP-1 antibody light chain variable region with a signal sequence
SEQ ID NO: 31: Amino acid sequence of the rtDNP-1 antibody light chain variable region without the signal sequence
SEQ ID NO: 32: Nucleotide sequence of the rtDNP-1 antibody heavy chain variable region with a signal sequence
SEQ ID NO: 33: Amino acid sequence of the rtDNP-1 antibody heavy chain variable region with a signal sequence
SEQ ID NO: 34: Amino acid sequence of the rtDNP-1 antibody heavy chain variable region without the signal sequence

The invention claimed is:

1. A method for treating pulmonary hypertension, comprising administering an effective amount of an antibody or an antibody fragment thereof which binds to the extracellular region of an interleukin-5 receptor (IL-5R) to inhibit an IL-5R-expressing cell,
wherein said antibody or antibody fragment thereof comprises a heavy chain variable (VH) domain containing 3 complementarity determining regions (CDRs), and a light chain variable (VL) domain containing 3 CDRs,
wherein the 3 CDRs on said VH domain comprise the amino acid sequences of SEQ ID NOs: 1-3, respectively, and the 3 CDRs on said VL domain comprise the amino acid sequences of SEQ ID NOs: 4-6, respectively.

2. The method according to claim 1, wherein the antibody has antibody-dependent cellular cytotoxic activity (ADCC activity).

3. The method according to claim 1, wherein the antibody has IL-5R-neutralizing activity.

4. The method according to claim 1, wherein the antibody inhibits group 2 innate lymphoid cell (ILC2)-dependent IL-5R-expressing cell growth.

5. The method according to claim 1, wherein the method is characterized by at least one of the following (i) to (iii):
    (i) the IL-5R-expressing cell is at least one cell of an eosinophil, a basophil, and a mast cell;
    (ii) the method inhibits the growth of a vascular smooth muscle cell; and
    (iii) the method inhibits pulmonary vascular remodeling.

6. The method according to claim 1, wherein the antibody is any one antibody selected from a monoclonal antibody and a recombinant antibody.

7. The method according to claim 1, wherein the antibody comprises a human Fc region or a human constant region.

8. The method according to claim 1, wherein said VH domain comprises the amino acid sequence of SEQ ID NO: 7, and said VL domain comprises the amino acid sequence of SEQ ID NO: 8.

9. The method according to claim 1, wherein said antibody comprises a heavy chain comprising the amino acid sequence of SEQ ID NO: 9, and a light chain comprising the amino acid sequence of SEQ ID NO: 10.

* * * * *

SEQUENCE LISTING

```
<160> NUMBER OF SEQ ID NOS: 34

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence, HCDR1

<400> SEQUENCE: 1

Ser Tyr Val Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic sequence, HCDR2

<400> SEQUENCE: 2

Tyr Ile Asn Pro Tyr Asn Asp Gly Thr Lys Tyr Asn Glu Arg Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Synthetic sequence, HCDR3

<400> SEQUENCE: 3

Glu Gly Ile Arg Tyr Tyr Gly Leu Leu Gly Asp Tyr
1               5                   10

<210> SEQ ID NO 4
<211> LENGTH: 11
<212> TYPE: PRT
<213> ORGANISM: Artificial Sequence
```

```
<220> FEATURE:
<223> OTHER INFORMATION: Synthetic sequence, LCDR1

<400> SEQUENCE: 4

Gly Thr Ser Glu Asp Ile Ile Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic sequence, LCDR2

<400> SEQUENCE: 5

His Thr Ser Arg Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic sequence, LCDR3

<400> SEQUENCE: 6

Gln Gln Gly Tyr Thr Leu Pro Tyr Thr
1               5

<210> SEQ ID NO 7
<211> LENGTH: 121
<212> TYPE: PRT
<213> ORGANISM: Artificial Sequence
<220> FEATURE:
<223> OTHER INFORMATION: Synthetic sequence, VH

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Arg Pro Gly Gln Gly Leu Ala Trp Met
        35                  40                  45

Gly Tyr Ile Asn Pro Tyr Asn Asp Gly Thr Lys Tyr Asn Glu Arg Phe
    50                  55                  60

Lys Gly Lys Val Thr Ile Thr Ser Asp Arg Ser Thr Ser Thr Val Tyr
65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
            100                 105                 110

Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Synthetic sequence, VL

<400> SEQUENCE: 8

Asp Ile Gln Met Thr Gln Ser Pro Ser Ser Leu Ser Ala Ser Val Gly
```

```
1               5                   10                  15
Asp Arg Val Thr Ile Thr Cys Gly Thr Ser Glu Asp Ile Ile Asn Tyr
                20                  25                  30

Leu Asn Trp Tyr Gln Gln Lys Pro Gly Lys Ala Pro Lys Leu Leu Ile
            35                  40                  45

Tyr His Thr Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys
                100                 105

<210> SEQ ID NO 9
<211> LENGTH: 451
<212> TYPE: PRT
<213> ORGANISM: Artificial Sequence
<220> FEATURE:
<223> OTHER INFORMATION: Synthetic sequence, Benralizumab heavy chain

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Ile His Trp Val Arg Gln Arg Pro Gly Gln Gly Leu Ala Trp Met
            35                  40                  45

Gly Tyr Ile Asn Pro Tyr Asn Asp Gly Thr Lys Tyr Asn Glu Arg Phe
        50                  55                  60

Lys Gly Lys Val Thr Ile Thr Ser Asp Arg Ser Thr Ser Thr Val Tyr
65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

```
                260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 10
<211> LENGTH: 155
<212> TYPE: PRT
<213> ORGANISM: Artificial Sequence
<220> FEATURE:
<223> OTHER INFORMATION: Synthetic sequence, Benralizumab light chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gly Thr Ser Glu Asp Ile Ile Asn Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln
145                 150                 155
```

```
<210> SEQ ID NO 11
<211> LENGTH: 21
<212> TYPE: DNA
<213> ORGANISM: Artificial Sequence
<220> FEATURE:
<223> OTHER INFORMATION: Synthetic sequence, rat kappa re

<400> SEQUENCE: 11
gccatcaatg ttccacttga c                                             21

<210> SEQ ID NO 12
<211> LENGTH: 22
<212> TYPE: DNA
<213> ORGANISM: Artificial Sequence
<220> FEATURE:
<223> OTHER INFORMATION: Synthetic sequence, rat gamma re

<400> SEQUENCE: 12
gtkacyggct cagggaaata gc                                            22

<210> SEQ ID NO 13
<211> LENGTH: 381
<212> TYPE: DNA
<213> ORGANISM: Artificial Sequence
<220> FEATURE:
<223> OTHER INFORMATION: Synthetic sequence, H7 VL DNA with signal
      sequence

<400> SEQUENCE: 13
atgggtgtcc ccactcagct cctggggttg ttgctactgt ggattacaga tgccatatgt    60
gacatccaga tgacacagtc tccagcttcc ctgtctgcat ctctgggaga aactgtcacc   120
atcgaatgtc gaacaagtga ggacatttac aatggtttag catggtatca gcagaagcca   180
gggaaatctc ctcagctcct gatctataat gcaaatagtt tgcatactgg ggtcccatca   240
cggttcagtg gcagtggatc tggtacacag tattctctca agataaacag tctgcaatct   300
gaagatgtcg caagttattg ctgtcaacag tattccaatt atcctttcac gttcggctca   360
gggacgaagt tggaaataaa a                                             381

<210> SEQ ID NO 14
<211> LENGTH: 127
<212> TYPE: PRT
<213> ORGANISM: Artificial Sequence
<220> FEATURE:
<223> OTHER INFORMATION: Synthetic sequence, H7 VL AA with signal
      sequence

<400> SEQUENCE: 14

Met Gly Val Pro Thr Gln Leu Leu Gly Leu Leu Leu Trp Ile Thr
1               5                   10                  15

Asp Ala Ile Cys Asp Ile Gln Met Thr Gln Ser Pro Ala Ser Leu Ser
            20                  25                  30

Ala Ser Leu Gly Glu Thr Val Thr Ile Glu Cys Arg Thr Ser Glu Asp
        35                  40                  45

Ile Tyr Asn Gly Leu Ala Trp Tyr Gln Gln Lys Pro Gly Lys Ser Pro
    50                  55                  60

Gln Leu Leu Ile Tyr Asn Ala Asn Ser Leu His Thr Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Ser Tyr Cys Cys Gln Gln Tyr Ser
            100                 105                 110
```

Asn Tyr Pro Phe Thr Phe Gly Ser Gly Thr Lys Leu Glu Ile Lys
            115                 120                 125

<210> SEQ ID NO 15
<211> LENGTH: 107
<212> TYPE: PRT
<213> ORGANISM: Artificial Sequence
<220> FEATURE:
<223> OTHER INFORMATION: Synthetic sequence, H7 VL AA without signal
      sequence

<400> SEQUENCE: 15

Asp Ile Gln Met Thr Gln Ser Pro Ala Ser Leu Ser Ala Ser Leu Gly
1               5                   10                  15

Glu Thr Val Thr Ile Glu Cys Arg Thr Ser Glu Asp Ile Tyr Asn Gly
            20                  25                  30

Leu Ala Trp Tyr Gln Gln Lys Pro Gly Lys Ser Pro Gln Leu Leu Ile
        35                  40                  45

Tyr Asn Ala Asn Ser Leu His Thr Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Ser Tyr Cys Cys Gln Gln Tyr Ser Asn Tyr Pro Phe
                85                  90                  95

Thr Phe Gly Ser Gly Thr Lys Leu Glu Ile Lys
            100                 105

<210> SEQ ID NO 16
<211> LENGTH: 429
<212> TYPE: DNA
<213> ORGANISM: Artificial Sequence
<220> FEATURE:
<223> OTHER INFORMATION: Synthetic sequence, H7 VH DNA with signal
      sequence

<400> SEQUENCE: 16
atgaaatgca gctggatcat cctcttcttg atggcactaa ctacagggt caactcagaa      60 gtccagctgc agcagtctgg ggctgagctt gggaaacctg gacctcagt caagttgtct    120 tgcaaggttt ctggctataa cattaagaat acctacatac actgggtgaa tcagaggcct    180
ggaaagggcc tggaatggat aggaaggatt gatcctgcaa atgaaatcc tatatatgct    240 gagaagttca aaacaaggc cacactgact gcagatacat cgtccaacac agcctacatg    300
caactcagcc aactgaaatc tgacgacaca gcaatctatt tttgtgctat gcatcggggg    360
catagtatgg gtcccggccc gtatgttatg gatgcctggg gtcaaggagc ttcagtcact    420
gtctcctca                                                           429

<210> SEQ ID NO 17
<211> LENGTH: 143
<212> TYPE: PRT
<213> ORGANISM: Artificial Sequence
<220> FEATURE:
<223> OTHER INFORMATION: Synthetic sequence, H7 VH AA with signal
      sequence

<400> SEQUENCE: 17

Met Lys Cys Ser Trp Ile Ile Leu Phe Leu Met Ala Leu Thr Thr Gly
1               5                   10                  15

Val Asn Ser Glu Val Gln Leu Gln Gln Ser Gly Ala Glu Leu Gly Lys
            20                  25                  30

Pro Gly Thr Ser Val Lys Leu Ser Cys Lys Val Ser Gly Tyr Asn Ile
         35                  40                  45

Lys Asn Thr Tyr Ile His Trp Val Asn Gln Arg Pro Gly Lys Gly Leu
     50                  55                  60

Glu Trp Ile Gly Arg Ile Asp Pro Ala Asn Gly Asn Pro Ile Tyr Ala
65                  70                  75                  80

Glu Lys Phe Lys Asn Lys Ala Thr Leu Thr Ala Asp Thr Ser Ser Asn
                 85                  90                  95

Thr Ala Tyr Met Gln Leu Ser Gln Leu Lys Ser Asp Asp Thr Ala Ile
             100                 105                 110

Tyr Phe Cys Ala Met His Arg Gly His Ser Met Gly Pro Gly Pro Tyr
             115                 120                 125

Val Met Asp Ala Trp Gly Gln Gly Ala Ser Val Thr Val Ser Ser
         130                 135                 140

<210> SEQ ID NO 18
<211> LENGTH: 124
<212> TYPE: PRT
<213> ORGANISM: Artificial Sequence
<220> FEATURE:
<223> OTHER INFORMATION: Synthetic sequence, H7 VH AA without signal
      sequence

<400> SEQUENCE: 18

Glu Val Gln Leu Gln Gln Ser Gly Ala Glu Leu Gly Lys Pro Gly Thr
1               5                   10                  15

Ser Val Lys Leu Ser Cys Lys Val Ser Gly Tyr Asn Ile Lys Asn Thr
             20                  25                  30

Tyr Ile His Trp Val Asn Gln Arg Pro Gly Lys Gly Leu Glu Trp Ile
         35                  40                  45

Gly Arg Ile Asp Pro Ala Asn Gly Asn Pro Ile Tyr Ala Glu Lys Phe
     50                  55                  60

Lys Asn Lys Ala Thr Leu Thr Ala Asp Thr Ser Ser Asn Thr Ala Tyr
65                  70                  75                  80

Met Gln Leu Ser Gln Leu Lys Ser Asp Asp Thr Ala Ile Tyr Phe Cys
                 85                  90                  95

Ala Met His Arg Gly His Ser Met Gly Pro Gly Pro Tyr Val Met Asp
             100                 105                 110

Ala Trp Gly Gln Gly Ala Ser Val Thr Val Ser Ser
         115                 120

<210> SEQ ID NO 19
<211> LENGTH: 45
<212> TYPE: DNA
<213> ORGANISM: Artificial Sequence
<220> FEATURE:
<223> OTHER INFORMATION: Synthetic sequence, VL fw

<400> SEQUENCE: 19
tcccgcgtcc tctagtgaca tccagatgac acagtctcca gcttc          45

<210> SEQ ID NO 20
<211> LENGTH: 44
<212> TYPE: DNA
<213> ORGANISM: Artificial Sequence
<220> FEATURE:
<223> OTHER INFORMATION: Synthetic sequence, VL re

<400> SEQUENCE: 20
gtgcagccac cgtacgtttt atttccaact tcgtccctga gccg    44

<210> SEQ ID NO 21
<211> LENGTH: 45
<212> TYPE: DNA
<213> ORGANISM: Artificial Sequence
<220> FEATURE:
<223> OTHER INFORMATION: Synthetic sequence, VH fw

<400> SEQUENCE: 21
aagggcgtgc agtgcgaagt ccagctgcag cagtctgggg ctgag    45

<210> SEQ ID NO 22
<211> LENGTH: 45
<212> TYPE: DNA
<213> ORGANISM: Artificial Sequence
<220> FEATURE:
<223> OTHER INFORMATION: Synthetic sequence, VH re

<400> SEQUENCE: 22
ggcccttggt gctagctgag gagacagtga ctgaagctcc ttgac    45

<210> SEQ ID NO 23
<211> LENGTH: 31
<212> TYPE: DNA
<213> ORGANISM: Artificial Sequence
<220> FEATURE:
<223> OTHER INFORMATION: Synthetic sequence, VL(CS) fw

<400> SEQUENCE: 23
agttattcct gtcaacagta ttccaattat c    31

<210> SEQ ID NO 24
<211> LENGTH: 29
<212> TYPE: DNA
<213> ORGANISM: Artificial Sequence
<220> FEATURE:
<223> OTHER INFORMATION: Synthetic sequence, VL(CS) re

<400> SEQUENCE: 24
ttgacaggaa taacttgcga catcttcag    29

<210> SEQ ID NO 25
<211> LENGTH: 381
<212> TYPE: DNA
<213> ORGANISM: Artificial Sequence
<220> FEATURE:
<223> OTHER INFORMATION: Synthetic H7 VL DNA for recombinant expression

<400> SEQUENCE: 25
atgggtgtcc ccactcagct cctggggttg ttgctactgt ggattacaga tgccatatgt    60
gacatccaga tgacacagtc tccagcttcc ctgtctgcat ctctgggaga aactgtcacc    120
atcgaatgtc gaacaagtga ggacatttac aatggtttag catggtatca gcagaagcca    180
gggaaatctc ctcagctcct gatctataat gcaaatagtt tgcatactgg ggtcccatca    240
cggttcagtg gcagtggatc tggtacacag tattctctca agataaacag tctgcaatct    300
gaagatgtcg caagttattg ctgtcaacag tattccaatt atcctttcac gttcggctca    360
gggacgaagt tggaaataaa a    381

<210> SEQ ID NO 26
<211> LENGTH: 381
<212> TYPE: DNA
<213> ORGANISM: Artificial Sequence
<220> FEATURE:
<223> OTHER INFORMATION: Synthetic H7(CS) VL DNA for recombinant
     expression

<400> SEQUENCE: 26

```
atgggtgtcc ccactcagct cctggggttg ttgctactgt ggattacaga tgccatatgt      60
gacatccaga tgacacagtc tccagcttcc ctgtctgcat ctctgggaga aactgtcacc     120
atcgaatgtc gaacaagtga ggacatttac aatggtttag catggtatca gcagaagcca     180
gggaaatctc ctcagctcct gatctataat gcaaatagtt tgcatactgg ggtcccatca     240
cggttcagtg gcagtggatc tggtacacag tattctctca agataaacag tctgcaatct     300
gaagatgtcg caagttattc ctgtcaacag tattccaatt atcctttcac gttcggctca     360
gggacgaagt tggaaataaa a                                               381
```

<210> SEQ ID NO 27
<211> LENGTH: 429
<212> TYPE: DNA
<213> ORGANISM: Artificial Sequence
<220> FEATURE:
<223> OTHER INFORMATION: Synthetic H7 or H7(CS) hIgG1 VH DNA for recombinant expression

<400> SEQUENCE: 27

```
atgaaatgca gctggatcat cctcttcttg atggcactaa ctacaggggt caactcagaa      60
gtccagctgc agcagtctgg ggctgagctt gggaaacctg ggacctcagt caagttgtct     120
tgcaaggttt ctggctataa cattaagaat acctacatac actgggtgaa tcagaggcct     180
ggaaagggcc tggaatggat aggaaggatt gatcctgcaa atggaaatcc tatatatgct     240
gagaagttca aaaacaaggc cacactgact gcagatacat cgtccaacac agcctacatg     300
caactcagcc aactgaaatc tgacgacaca gcaatctatt tttgtgctat gcatcggggg     360
catagtatgg gtcccggccc gtatgttatg gatgcctggg gtcaaggagc ttcagtcact     420
gtctcctca                                                             429
```

<210> SEQ ID NO 28
<211> LENGTH: 429
<212> TYPE: DNA
<213> ORGANISM: Artificial Sequence
<220> FEATURE:
<223> OTHER INFORMATION: Synthetic H7 or H7(CS) hIgG1(N297A) VH DNA

<400> SEQUENCE: 28

```
atgaaatgca gctggatcat cctcttcttg atggcactaa ctacaggggt caactcagaa      60
gtccagctgc agcagtctgg ggctgagctt gggaaacctg ggacctcagt caagttgtct     120
tgcaaggttt ctggctataa cattaagaat acctacatac actgggtgaa tcagaggcct     180
ggaaagggcc tggaatggat aggaaggatt gatcctgcaa atggaaatcc tatatatgct     240
gagaagttca aaaacaaggc cacactgact gcagatacat cgtccaacac agcctacatg     300
caactcagcc aactgaaatc tgacgacaca gcaatctatt tttgtgctat gcatcggggg     360
catagtatgg gtcccggccc gtatgttatg gatgcctggg gtcaaggagc ttcagtcact     420
gtctcctca                                                             429
```

<210> SEQ ID NO 29
<211> LENGTH: 396
<212> TYPE: DNA
<213> ORGANISM: Artificial Sequence
<220> FEATURE:

<223> OTHER INFORMATION: Synthetic sequence, rtDNP-1 VL DNA with signal
      sequence

<400> SEQUENCE: 29

| | | |
|---|---|---|
| atgaatctgc cgtgcatct gctggtgctg ctgctgttct ggatccccgc ctcccgcggg | 60 |
| gatgtggtga tgactcagac tcccgtgtcc ctgcccgtgt ccctgggggg gcaggcctcc | 120 |
| atctcctgtc gctcctccca gtccctggcc aattcctatg gaatactta tctgtcctgg | 180 |
| tatctgcaga agcccgggca gtcccccag ctgctgatct atcgcgtgtc caatactttc | 240 |
| tccggggtgc ccgatcgctt ctccgggtcc gggtccggga ctgatttcac tctgaagatc | 300 |
| tcccgcgtgg agcccgagga tctgggggat tattattgtc tgcaggggac tcatcagccc | 360 |
| tatactttcg gggccgggac taagctggag ctgaag | 396 |

<210> SEQ ID NO 30
<211> LENGTH: 132
<212> TYPE: PRT
<213> ORGANISM: Artificial Sequence
<220> FEATURE:
<223> OTHER INFORMATION: Synthetic sequence, rtDNP-1 VL AA with signal
      sequence

<400> SEQUENCE: 30

Met Asn Leu Pro Val His Leu Leu Val Leu Leu Leu Phe Trp Ile Pro
1               5                   10                  15

Ala Ser Arg Gly Asp Val Val Met Thr Gln Thr Pro Val Ser Leu Pro
            20                  25                  30

Val Ser Leu Gly Gly Gln Ala Ser Ile Ser Cys Arg Ser Ser Gln Ser
        35                  40                  45

Leu Ala Asn Ser Tyr Gly Asn Thr Tyr Leu Ser Trp Tyr Leu Gln Lys
    50                  55                  60

Pro Gly Gln Ser Pro Gln Leu Leu Ile Tyr Arg Val Ser Asn Thr Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Pro Glu Asp Leu Gly Asp Tyr Tyr
            100                 105                 110

Cys Leu Gln Gly Thr His Gln Pro Tyr Thr Phe Gly Ala Gly Thr Lys
        115                 120                 125

Leu Glu Leu Lys
    130

<210> SEQ ID NO 31
<211> LENGTH: 112
<212> TYPE: PRT
<213> ORGANISM: Artificial Sequence
<220> FEATURE:
<223> OTHER INFORMATION: Synthetic sequence, rtDNP-1 VL AA without
      signal sequence

<400> SEQUENCE: 31

Asp Val Val Met Thr Gln Thr Pro Val Ser Leu Pro Val Ser Leu Gly
1               5                   10                  15

Gly Gln Ala Ser Ile Ser Cys Arg Ser Ser Gln Ser Leu Ala Asn Ser
            20                  25                  30

Tyr Gly Asn Thr Tyr Leu Ser Trp Tyr Leu Gln Lys Pro Gly Gln Ser
        35                  40                  45

Pro Gln Leu Leu Ile Tyr Arg Val Ser Asn Thr Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Pro Glu Asp Leu Gly Asp Tyr Tyr Cys Leu Gln Gly
                85                  90                  95

Thr His Gln Pro Tyr Thr Phe Gly Ala Gly Thr Lys Leu Glu Leu Lys
            100                 105                 110

<210> SEQ ID NO 32
<211> LENGTH: 405
<212> TYPE: DNA
<213> ORGANISM: Artificial Sequence
<220> FEATURE:
<223> OTHER INFORMATION: Synthetic sequence, rtDNP-1 VH DNA with signal
      sequence

<400> SEQUENCE: 32
atgatggtgc tgtccctgct gtatctgctg actgccctgc ccgggatcct gtccgaggtg      60
cagctgcagg agtccgggcc cgggctggtg aagccctccc agtccctgtc cctgacttgt     120
tccgtgactg gtattccat cacttccggg tattggaatt ggatccgcaa gttccccggg      180
aataagatgg agtggatcgg gtatatctcc tattccgggt ccacttatta taatccctcc     240
ctgaagtccc gcatctccat cactcgcgat acttccaaga atcagttctt cctgcagctg     300
aattccgtga ctactgagga tactgccact tattattgtg cccgctgggg ggtgcgccat     360
tatttcgatt attgggggca gggggtgatg gccactgtgt cctcc                     405

<210> SEQ ID NO 33
<211> LENGTH: 135
<212> TYPE: PRT
<213> ORGANISM: Artificial Sequence
<220> FEATURE:
<223> OTHER INFORMATION: Synthetic sequence, rtDNP-1 VH AA with signal
      sequence

<400> SEQUENCE: 33

Met Met Val Leu Ser Leu Leu Tyr Leu Leu Thr Ala Leu Pro Gly Ile
1               5                   10                  15

Leu Ser Glu Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Ser Gly Tyr Trp Asn Trp Ile Arg Lys Phe Pro Gly Asn Lys Met Glu
    50                  55                  60

Trp Ile Gly Tyr Ile Ser Tyr Ser Gly Ser Thr Tyr Tyr Asn Pro Ser
65                  70                  75                  80

Leu Lys Ser Arg Ile Ser Ile Thr Arg Asp Thr Ser Lys Asn Gln Phe
                85                  90                  95

Phe Leu Gln Leu Asn Ser Val Thr Thr Glu Asp Thr Ala Thr Tyr Tyr
            100                 105                 110

Cys Ala Arg Trp Gly Val Arg His Tyr Phe Asp Tyr Trp Gly Gln Gly
        115                 120                 125

Val Met Ala Thr Val Ser Ser
    130                 135

<210> SEQ ID NO 34
<211> LENGTH: 117
<212> TYPE: PRT
<213> ORGANISM: Artificial Sequence
<220> FEATURE:

```
<223> OTHER INFORMATION: Synthetic sequence, rtDNP-1 VH AA without
      signal sequence

<400> SEQUENCE: 34

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Trp Asn Trp Ile Arg Lys Phe Pro Gly Asn Lys Met Glu Trp Ile
            35                  40                  45

Gly Tyr Ile Ser Tyr Ser Gly Ser Thr Tyr Tyr Asn Pro Ser Leu Lys
        50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Arg Trp Gly Val Arg His Tyr Phe Asp Tyr Trp Gly Gln Gly Val Met
            100                 105                 110

Ala Thr Val Ser Ser
            115
```